US008980638B2

(12) United States Patent
Jiang

(10) Patent No.: US 8,980,638 B2
(45) Date of Patent: Mar. 17, 2015

(54) USE OF IMP3 AS A PROGNOSTIC MARKER FOR CANCER

(71) Applicant: University of Massachusetts, Boston, MA (US)

(72) Inventor: Zhong Jiang, Northborough, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/718,022

(22) Filed: Dec. 18, 2012

(65) Prior Publication Data
US 2013/0197514 A1 Aug. 1, 2013

Related U.S. Application Data

(63) Continuation of application No. 12/690,647, filed on Jan. 20, 2010, now abandoned, which is a continuation-in-part of application No. 11/758,382, filed on Jun. 5, 2007, now abandoned.

(60) Provisional application No. 60/811,702, filed on Jun. 6, 2006, provisional application No. 60/813,216, filed on Jun. 12, 2006.

(51) Int. Cl.
| | |
|---|---|
| *C12Q 1/00* | (2006.01) |
| *G01N 33/00* | (2006.01) |
| *G01N 33/48* | (2006.01) |
| *G01N 33/53* | (2006.01) |
| *G01N 33/566* | (2006.01) |
| *G01N 33/567* | (2006.01) |
| *G01N 33/574* | (2006.01) |
| *A61B 17/00* | (2006.01) |
| *A61B 18/04* | (2006.01) |
| *G01N 33/68* | (2006.01) |
| *C12Q 1/68* | (2006.01) |

(52) U.S. Cl.
CPC .......... *G01N 33/6893* (2013.01); *C12Q 1/6886* (2013.01); *C12Q 2600/106* (2013.01); *C12Q 2600/112* (2013.01); *C12Q 2600/118* (2013.01); *C12Q 2600/158* (2013.01)
USPC ............... 436/64; 436/63; 436/86; 436/174; 436/501; 436/503; 435/4; 435/6.1; 435/6.11; 435/6.14; 435/6.19; 435/7.21; 435/7.23; 606/1; 606/32

(58) Field of Classification Search
CPC .......... C12Q 1/00; C12Q 1/68; C12Q 1/6876; C12Q 1/6883; C12Q 2600/00; C12Q 2600/118; C12Q 2600/158; G01N 1/00; G01N 33/00; G01N 33/48; G01N 33/50; G01N 33/5005; G01N 33/68; G01N 33/6893
USPC ......... 435/4, 6.1, 6.11, 6.14, 6.19, 7.21, 7.23; 436/63, 64, 86, 174, 501, 503; 606/1, 606/32

See application file for complete search history.

(56) References Cited

U.S. PATENT DOCUMENTS

| | | | |
|---|---|---|---|
| 2005/0196796 A1* | 9/2005 | Mousses et al. | 435/6 |
| 2005/0244880 A1* | 11/2005 | Kallioniemi et al. | 435/6 |
| 2009/0035763 A1* | 2/2009 | Reid et al. | 435/6 |
| 2009/0053731 A1* | 2/2009 | Sojka et al. | 435/7.1 |

OTHER PUBLICATIONS

Askalani et al. Immunohistochemical localization and monoclonal antibodies quantitiative measurement of carcionembryonic antigen (CEA) in cervical neoplasia. The Internet Journal of Gynecology and Obstetrics 2(1): 1-6, 2003.*
Istvanic et al. Spectrum of KOC (K homology domain containing protein over-expressed in cancer) immunostaining among carcinomas of different sites. Mod. Pathol. 18(15): 296A-302A, Feb. 2005.*
Huang et al. A comparison between loop electrosurgical excision procedure and cold knife conization for treatment of cervical dysplasia: residual disease in subsequent hysterectomy specimen. Gynecologic Oncology 73: 12-15, 1999.*
Li et al. Comparison of p16 and KOC expression in benign glandular epithelium and adenocarcinoma in situ of the uterine cervix. Laboratory Investigation 86. Supplement 1: 187A, Abstract 865, Jan. 2006.*
Askalani et al., The Internet Journal of Gynecology and Obstetrics 2(1):1-6 (2003).
Brants Jr. et al., "Differential regulation of the insulin-like growth factor II mRNA-binding protein genes by architectural transcription factor HMGA2," FEBS Lett. 569(1-3):277-83 (2004).
Cheville JC, et al., "Comparisons of outcome and prognostic features among histologic subtypes of renal cell carcinoma" American Journal of Surgical Pathology; 27:612-624 (2003).
Chow WH, et al., "Rising incidence of renal cell cancer in the United States," Jama; 281(17): 1628-31 (1999).
Cohen HT, et al., "Renal-cell carcinoma," New England Journal of Medicine, 353(23):2477-90 (2005).
Freeman JA, et al., "Radical cystectomy for high risk patients with superficial bladder cancer in the era of orthotopic urinary reconstruction," Cancer, 76: 833-839 (1995).
Habuchi T, et al., "Prognostic markers for bladder cancer: International Consensus Panel on bladder tumor markers," Urology, 66: 64-74 (2005).
Hammer et al., "Expression of IGF-II mRNA-binding proteins (IMPs) in gonads and testicular cancer," Reproduction, 130:203-212 (2005).
Herr HW, et al., "Does early cystectomy improve the survival of patients with high risk superficial bladder tumors?," Journal of Urology, 166: 1296-1299 (2001).

(Continued)

*Primary Examiner* — Alana Harris Dent
(74) *Attorney, Agent, or Firm* — Fish & Richardson P.C.

(57) ABSTRACT

Provided herein are methods and compositions for the prognostic evaluation of a patient suspected of having, or having, cancer by assessing the expression of IMP3 in a biological sample of a patient. Methods can be used at the time of initial diagnosis of malignant tumors to identify a group of patients with a high potential to develop progression or metastasis later. Therefore, methods not only are able to provide very useful prognostic information for patients but also can help clinicians to select a candidate patient likely to benefit from early and aggressive cancer therapy. Methods and compositions for the treatment of cancer associated with expression of IMP3 are also provided.

9 Claims, 13 Drawing Sheets

(56) References Cited

OTHER PUBLICATIONS

Holzbeierlein JM, et al., "Surgical management of noninvasive bladder cancer (stages TA/T1/CIS)," Urologic Clinics of North America, 27: 15-24 (2000).
Istvanic et al., Mod. Pathol. 18(15): 296A-302A (2005).
Jemal A, et al., "Cancer Statistics, 2005," CA: A Cancer Journal for Clinicians, 55(4):10-30 (2005).
Jiang et al., "Analysis of RNA-binding protein IMP3 to predict metastasis and prognosis of renal-cell carcinoma: a retrospective study," Lancet Oncol., 7:556-564 (2006).
Jiang et al., "Combination of quantitative IMP3 and tumor stage: a new system to predict metastasis for patients with localized renal cell carcinomas," Clin. Cancer Res., 14(17):5579-5584 (2008).
Joudi FN, et al., "Contemporary management of superficial bladder cancer in the United States: a pattern of care analysis," Urology, 62: 1083-1088 (2003).
Kirkali Z, et al., "J. Bladder cancer: epidemiology, staging and grading, and diagnosis," Urology, 66: 4-34 (2005).
Kovacs G, et al., "The Heidelberg classification of renal cell tumors," Journal of Pathology, 183: 131-133 (1997).
Lam JS, et al "Renal cell carcinoma 2005: new frontiers in staging, prognostication and targeted molecular therapy," Journal of Urology, 173(6):1853-62 (2005).
Li C, et al., "Expression of a novel oncofetal mRNA-binding protein IMP3 in endometrial carcinomas: diagnostic significance and clinicopathologic correlations," Mod Pathol., 20(12):1263-1268 (2007).
Li C, et al., "IMP3 is a novel biomarker for adenocarcinoma in situ of the uterine cervix: an immunohistochemical study in comparison with p16(INK4a) expression," Mod Pathol., 20(2):242-7 (2007).
Li et al., Laboratory Investigation 86 (Supplement 1: 187A, Abstract 865) (2006).
Liao B, et al., "The RNA-binding Protein IMP-3 Is a Translational Activator of Insulin-like Growth Factor II Leader-3 mRNA during Proliferation of Human K562 Leukemia Cells," J. Biol. Chem., 280(18): 18517-18524 (2005).
Lohse CM, et al., "A review of prognostic pathologic features and algorithms for patients treated surgically for renal cell carcinoma," Clinics in Laboratory Medicine, 25:433-464 (2005).
Malats N, et al., "P53 as a prognostic marker for bladder cancer: a meta-analysis and review," Lancet Oncology, 6:678-686 (2005).
Monk D., et al., "Characterisation of the growth regulating gene IMP3, a candidate for Silver-Russell syndrome," Journal of Medical Genetics, 39:575-581 (2002).
Mori H, et al., "Expression of mouse igf2 mRNA-binding protein 3 and its implications for the developing central nervous system," J Neurosci Res., 64(2):132-43 (2001).
Motzer RJ, et al., "Renal-cell carcinoma," New England Journal of Medicine, 335(12):865-875 (1996).
Mueller F, et al., "KOC is a novel molecular indicator of malignancy," Br J Cancer, 88(5):699-701 (2003).
Mueller-Pillasch F, et al., "Cloning of a gene highly overexpressed in cancer coding for a novel KH-domain containing protein," Oncogene, 14: 2729-2733 (1997).
Mueller-Pillasch F, et al., "Expression of the highly conserved RNA binding protein KOC in embryogenesis," Mechanisms of Development, 88: 95-99 (1999).
Nielsen J, et al., "A family of insulin-like growth factor II mRNA-binding proteins represses translation in late development," Molecular & Cellular Biology, 19:1262-1270 (1999).
Rabinovitch RA, et al., "Patterns of failure following surgical resection of renal cell carcinoma: implications for adjuvant local and systemic therapy" Journal of Clinical Oncology, 12(1):206-212 (1994).
Ramakrishnan C, et al., "Steroid hormone responsiveness of a family of closely related mouse proviral elements;" Mamm Genome., 8(11):811-7 (1997).
Sandock OS, et al. "A new protocol for the followup of renal cell carcinoma based on pathological stage," Journal of Urology 154(1):28-31 (1995).
Sengupta S, et al., "The management of superficial transitional cell carcinoma of the bladder," Urology, 67: 48-54 (2006).
Simon R, et al., "Extrapulmonary small cell carcinomas express K homology domain containing protein overexpressed in cancer, but carcinoid tumors do not," Hum Pathol., 38(8): 1178-1183 (2007).
Storkel S, et al., "Classification of renal cell carcinoma: Workgroup No. 1. Union Internationale Contre le Cancer (UICC) and the American Joint Committee on Cancer (AJCC)," Cancer, 80:987-989 (1997).
Thrasher JB, et al., "Clinical Variables which Serve as Predictors of Cancer-Specific Survival among Patients Treated with Radical Cystectomy for Transitional Cell Carcinoma of the Bladder and Prostate," Clinical Prognosticators in Bladder Cancer, 73(6):1708-1715 (1994).
Tsui KH, et al., "Prognostic indicators for renal cell carcinoma: a multivariate analysis of 643 patients using the revised 1997 TNM staging criteria." Journal of Urology, 163(4):1090-1095 (2000).
Vikesaa J, et al, "RNA-binding IMPs promote cell adhesion and invadopodia formation," EMBO Journal, 25(7):1456-1468 (2006).
Wang T, et al., "L523S, an RNA-binding protein as a potential therapeutic target for lung cancer," British Journal of Cancer, 88:887-894 (2003).
Wehner KA, et al., "Components of an interdependent unit within the SSU processome regulate and mediate its activity," Mol Cell Biol., 22(20):7258-7267 (2002).
Xu H, et al., "High-grade neuroendocrine carcinomas of the lung express K homology domain containing protein overexpressed in cancer but carcinoid tumors do not," Hum Pathol., 38(4 ):555-563 (2007).
Yaniv K, et al., "The involvement of a conserved family of RNA binding proteins in embryonic development and carcinogenesis," Gene, 287:49-54 (2002).
Yantiss RK, et al., "KOC (K homology domain containing protein overexpressed in cancer): a novel molecular marker that distinguishes between benign and malignant lesions of the pancreas," American Journal of Surgical Pathology, 29:188-195 (2005).
Zhang JY, et al., "Autoimmune responses to mRNA binding proteins p62 and Koc in diverse Malignancies," Clin Immunol., 100(2):149-56 (2001).
Zhao H, et al., "Expression of K homology domain containing protein overexpressed in cancer in pancreatic FNA for diagnosing adenocarcinoma of pancreas," Diagn Cytopathol., 35(11):700-4 (2007).
Zhao H, et al., "Gene Expression Profiling Predicts Survival in Conventional Renal Cell Carcinoma;" PLoS Med, 3(1)(e13): 0115-0124 (2006).
International Search Report for PCT/US07/70412, Jun. 18, 2008.

* cited by examiner

IMP3 Positive    IMP3 Positive    IMP3 Negative

A Stage I
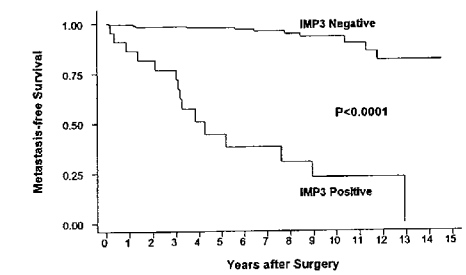
B Stage I
FIGURE 5
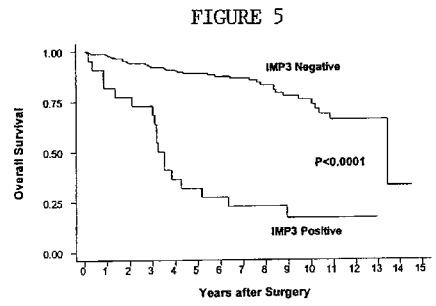
C Stage II
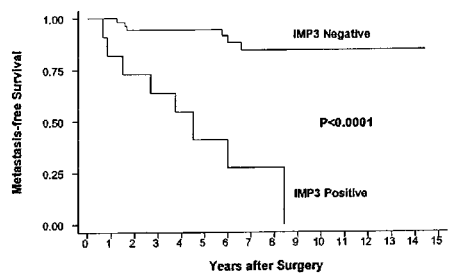
D Stage II
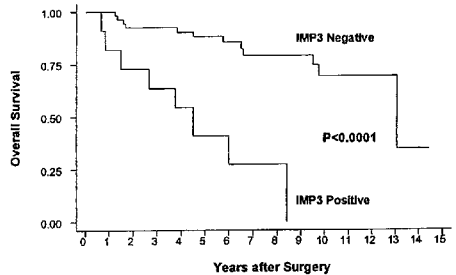
E Stage III
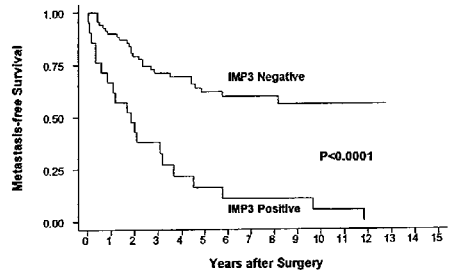
F Stage III
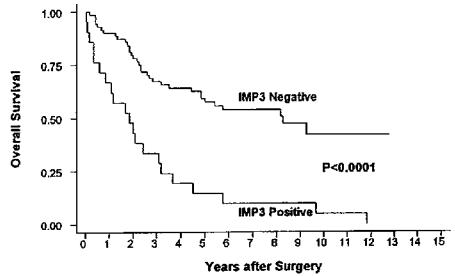

SEQUENCE LISTING

```
<160> NUMBER OF SEQ ID NOS: 8

<210> SEQ ID NO 1
<211> LENGTH: 1740
<212> TYPE: DNA
<213> ORGANISM: Homo sapiens

<400> SEQUENCE: 1
atgaacaaac tgtatatcgg aaacctcagc gagaacgccg cccctcgga cctagaaagt      60 atcttcaagg acgccaagat cccggtgtcg ggacccttcc tggtgaagac tggctacgcg     120
ttcgtggact gcccggacga gagctgggcc ctcaaggcca tcgaggcgct ttcaggtaaa     180
atagaactgc acgggaaacc catagaagtt gagcactcgg tcccaaaaag gcaaaggatt     240
cggaaacttc agatacgaaa tatcccgcct catttacagt gggaggtgct ggatagttta     300
ctagtccagt atggagtggt ggagagctgt gagcaagtga acactgactc ggaaactgca     360
gttgtaaatg taacctattc cagtaaggac caagctagac aagcactaga caaactgaat     420
ggatttcagt tagagaattt caccttgaaa gtagcctata tccctgatga aatggccgcc     480
cagcaaaacc ccttgcagca gccccgaggt cgccggggc ttgggcagag gggctcctca     540 aggcagggt ctccaggatc cgtatccaag cagaaaccat gtgatttgcc tctgcgcctg     600
ctggttccca cccaatttgt tggagccatc ataggaaaag aaggtccac cattcggaac     660 atcaccaaac agacccagtc taaaatcgat gtccaccgta agaaaatgc gggggctgct     720 gagaagtcga ttactatcct ctctactcct gaaggcacct ctgcggcttg taagtctatt     780
ctggagatta tgcataagga agctcaagat ataaaattca cagaagagat ccccttgaag     840 atttagctc ataataactt tgttggacgt cttattggta aagaaggaag aaatcttaaa     900
aaaattgagc aagacacaga cactaaaatc acgatatctc cattgcagga attgacgctg     960
```

-continued

```
tataatccag aacgcactat tacagttaaa ggcaatgttg agacatgtgc caaagctgag    1020
gaggagatca tgaagaaaat cagggagtct tatgaaaatg atattgcttc tatgaatctt    1080
caagcacatt taattcctgg attaaatctg aacgccttgg gtctgttccc acccacttca    1140
gggatgccac ctcccacctc agggcccct tcagccatga ctcctcccta cccgcagttt    1200
gagcaatcag aaacggagac tgttcatctg tttatcccag ctctatcagt cggtgccatc    1260
atcggcaagc agggccagca catcaagcag ctttctcgct tgctggagc ttcaattaag    1320
attgctccag cggaagcacc agatgctaaa gtgaggatgg tgattatcac tggaccacca    1380
gaggctcagt tcaaggctca gggaagaatt tatggaaaaa ttaaagaaga aactttgtt     1440
agtcctaaag aagaggtgaa acttgaagct catatcagag tgccatcctt tgctgctggc    1500
agagttattg gaaaaggagg caaaacggtg aatgaacttc agaatttgtc aagtgcagaa    1560
gttgttgtcc ctcgtgacca gacacctgat gagaatgacc aagtggttgt caaaataact    1620
ggtcacttct atgcttgcca ggttgcccag agaaaaattc aggaaattct gactcaggta    1680
aagcagcacc aacaacagaa ggctctgcaa agtggaccac tcagtcaag acggaagtaa     1740
```

<210> SEQ ID NO 2
<211> LENGTH: 579
<212> TYPE: PRT
<213> ORGANISM: Homo sapiens

<400> SEQUENCE: 2

```
Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240
```

```
Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Val Pro Arg Asp Gln Thr
        515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
gctaaagtga ggatggtgat tatcact                                      27

<210> SEQ ID NO 4
```

```
<211> LENGTH: 32
<212> TYPE: DNA
<213> ORGANISM: Artificial
<220> FEATURE:
<223> OTHER INFORMATION: Primer

<400> SEQUENCE: 4
actaacaaag ttttcttctt taatttttcc at                                    32

<210> SEQ ID NO 5
<211> LENGTH: 29
<212> TYPE: DNA
<213> ORGANISM: Artificial
<220> FEATURE:
<223> OTHER INFORMATION: Probe

<400> SEQUENCE: 5
accagaggct cagttcaagg ctcagggaa                                        29

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
gaaggtgaag gtcggagtc                                                   19

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
gaagatggtg atgggatttc                                                  20

<210> SEQ ID NO 8
<211> LENGTH: 20
<212> TYPE: DNA
<213> ORGANISM: Artificial
<220> FEATURE:
<223> OTHER INFORMATION: Probe

<400> SEQUENCE: 8
caagcttccc gttctcagcc                                                  20
```

USE OF IMP3 AS A PROGNOSTIC MARKER FOR CANCER

RELATED APPLICATIONS

This application is a continuation of U.S. patent application Ser. No. 12/690,647 filed Jan. 20, 2010, which is a continuation-in-part of U.S. Ser. No. 11/758,382, which was filed on Jun. 5, 2007, and claims the benefit of priority to U.S. provisional applications 60/811,702 filed Jun. 6, 2006 and 60/813,216, filed Jun. 12, 2006, all of which are specifically incorporated herein by reference in their entirety.

BACKGROUND

In spite of numerous advances in medical research, cancer remains a leading cause of death in the United States. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site and/or metastases. The etiology, diagnosis and ablation of cancer remain a central focus for medical research and development.

While different forms of cancer have different properties, one factor which many cancers share is the ability to metastasize. Distant metastasis of all malignant tumors remains the primary cause of death in patients with the disease. Patients with metastatic disease are typically treated with systemic therapy, which is associated with substantial toxicity. Unless the patient presents with metastatic disease, clinical observation is typically used to prognose the disease following surgical resection. Currently, the methods to determine prognosis and select patients for adjuvant therapy rely mainly on pathological and clinical staging. However, it is very difficult to predict which localized tumor will eventuate in distant metastasis.

Since the chance for complete remission of cancer is, in most cases, greatly enhanced by accurate prognosis, it is desirable that physicians be able to determine the metastatic potential of tumors. However, the metastatic potential of localized cancers is often unpredictable. The development of methods that permit rapid and accurate detection of many forms of cancers continues to challenge the medical community. Thus a major problem in the treatment of cancer remains detection and prognosis, which enables appropriate therapeutic treatment resulting in successful treatment in many cases. Therefore, there is a great need for the identification of biomarkers that can accurately distinguish localized tumors with a high probability of metastasis from those that will remain indolent. Using such biomarkers, one can predict the patient's prognosis and can effectively target the individuals who would most likely benefit from adjuvant therapy.

SUMMARY

The present invention is based at least in part on the finding that the expression of IMP3 is strongly associated with tumor metastasis and poor prognosis. IMP3 thus serves as an independent prognostic biomarker to predict cancer metastasis and a potential target protein to treat metastatic cancer.

Provided herein are methods for predicting the prognosis of a subject having a cancerous tumor. The method may comprise determining the level of IMP3 in a cancerous tumor of a subject, wherein a higher level of IMP3 in the cancerous tissue of the subject, e.g., relative to that in a control indicates that the prognosis of the subject is poor, whereas an undetectable or a lower or similar level of IMP3 in the cancerous tissue of the subject relative to that in the control indicates that the prognosis of the subject is good. A method may also comprise determining the presence of IMP3 in a cancerous tissue in a subject, wherein the presence of IMP3 in the cancerous tissue indicates that the prognosis of the subject is poor. Determining the level of IMP3 may comprise determining the level of IMP3 protein, e.g., by immunohistochemical staining, which may be followed by computerized image analysis for quantitative immunohistochemistry. A control may be the level of IMP3 in non-cancerous cells of the same origin as those of the cancerous tumor or the level of IMP3 in cells of a cancerous tumor that has a good prognosis. The cancerous tumor may be a renal tumor or a urinary bladder tumor. The method further comprises first obtaining a biopsy of a cancerous tumor of the subject.

A prognostic method may also comprise determining the presence or level of IMP3 and evaluate another prognostic factor, e.g., the stage of the tumor.

Also provided herein are methods for treating a subject having a cancerous tumor. A method may comprise (i) determining the level of IMP3 in the cancerous tumor of a subject; and (ii) if the level of IMP3 in the cancerous tumor of a subject is more similar to that of a cancerous tumor of a subject having a poor prognosis rather than that of a subject having a good prognosis, treating the subject aggressively, whereas if the level of IMP3 in the cancerous tumor of a subject is more similar to that of a cancerous tumor of a subject having a good prognosis rather than that of a subject having a poor prognosis, treating the subject less aggressively. Instead of determining a level of IMP3 and comparing it to a control, a method may comprise determining the presence of IMP3, wherein the presence of IMP3 indicates that the subject should be treated aggressively.

Further provided herein are kits, e.g., kits comprising one or more agents for detecting the level of IMP3. A kit may also comprise a control. The agent for detecting the level of IMP3 may be an antibody or a variant, e.g., a fragment, thereof. A control may be the level of IMP3 in a cancerous tumor having a good prognosis or it may be a sample of a healthy subject. A kit may also comprise one or more other biomarkers or reagents for evaluating other prognostic factors.

Other methods provided herein are methods for monitoring the progression of a cancer in a subject. A method may comprise monitoring the level of IMP3 in a cancerous tumor of the subject over time, wherein an increase in the level of IMP3 in a cancerous tumor of the subject indicates that the cancer is progressing.

Therapeutic methods are also provided herein. An exemplary method for treating a subject having a cancer associated with high levels of IMP3, comprises administering to the subject a therapeutically effective amount of an agent that reduces the level or activity of IMP3, such as by directly targeting IMP3 protein or its expression or by targeting an IMP3 target, such as insulin-like growth factor II (IGF-II).

BRIEF DESCRIPTION OF THE DRAWINGS

FIG. 5. Kaplan-Meier analysis of metastasis-free and overall survivals in stage I patients (n=216, A and B), stage II patients (n=64, C and D) and stage III patients (n=91, E and F) according to IMP3 status (positive verses negative) with localized primary RCCs assessed by immunohistochemical analysis. P values were calculated by using the log-rank test.

DETAILED DESCRIPTION

Definitions

Figure 1:
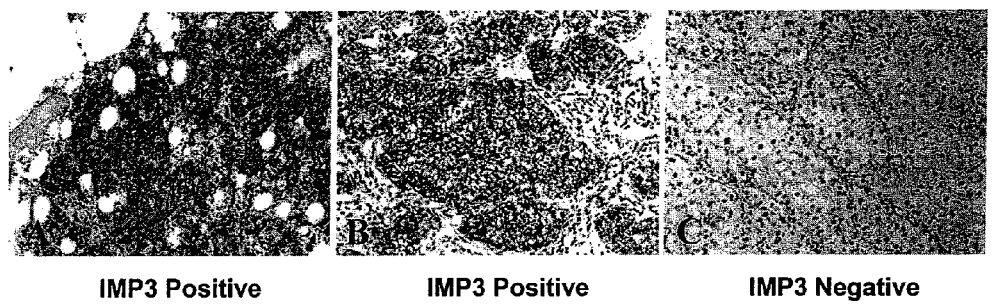
FIG. 1. Expression of IMP3 in primary and metastatic renal cell carcinomas. Immunohistochemical stains for IMP3 showing that metastatic RCC in the bone (A) and primary RCC with subsequent development of metastasis (B) were positive for IMP3 while primary RCC without metastasis (C) were negative for IMP3.

"Cancers of epithelial origin" refers to "carcinomas" that arise from epithelial cells which include, but are not limited to, skin cancer, such as squamous cell and basal cell cancers, lung cancer, breast cancer, prostate cancer, renal cell carcinoma, liver cancer, urinary bladder cancer, ovarian cancer, cervical cancer, endometrial cancer, gastrointestinal cancers including esophageal cancer, small bowel cancer, stomach cancer, colon cancer and other known cancers that effect epithelial cells throughout the body.

The term "aggressive" or "invasive" with respect to cancer refers to the proclivity of a tumor for expanding beyond its boundaries into adjacent tissue (Darnell, J. (1990), Molecular Cell Biology, Third Ed., W. H. Freeman, N.Y.). Invasive cancer can be contrasted with organ-confined cancer wherein the tumor is only in a particular organ. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located.

The term "metastasis", as used herein, refers to the condition of spread of cancer from the organ of origin to additional distal sites in the patient. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

A "biological sample" refers to a sample of biological material obtained from a subject, preferably a human subject, including a tissue, a tissue sample, a cell sample, a tumor sample, and a biological fluid, e.g., blood, urine, and a nipple aspirate. A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy and an endoscopic biopsy.

An "isolate" of a biological sample (e.g., an isolate of a tissue or tumor sample) refers to a material or composition (e.g., a biological material or composition) which has been separated, derived, extracted, purified or isolated from the sample and preferably is substantially free of undesirable compositions and/or impurities or contaminants associated with the biological sample.

A "tissue sample" includes a portion, piece, part, segment, or fraction of a tissue which is obtained or removed from an intact tissue of a subject, preferably a human subject.

A "tumor sample" includes to a portion, piece, part, segment, or fraction of a tumor, for example, a tumor which is obtained or removed from a subject (e.g., removed or extracted from a tissue of a subject), preferably a human subject.

A "tumor" refers to an abnormal growth of cells.

A "primary tumor" is a tumor appearing at a first site within the subject and can be distinguished from a "metastatic tumor" which appears in the body of the subject at a remote site from the primary tumor.

A "patient" refers to any warm-blooded animal, preferably a human.

Prognostic and Diagnostic Biomarker and Methods

The present invention provides methods for predicting or determining the prognosis, e.g., likelihood of metastasis or aggressive behavior, in subjects with malignant tumors. A method may comprise measuring the level of expression of IMP3 present in a biological sample obtained from a patient and comparing the observed level with one or a range of IMP3 levels normally found in biological samples (of the same type) of healthy individuals. A high level of IMP3 expression is indicative of a greater potential for metastatic activity or aggressive behavior and corresponds to a poor prognosis, while very low or undetectable levels indicate that the tumor is less aggressive and correspond to a better prognosis.

An exemplary method, e.g., for predicting the prognosis of a subject having a cancerous tumor, comprises determining the presence of IMP3 in a cancerous tumor of a subject, wherein the presence of IMP3 in the cancerous tissue of the subject indicates that the prognosis of the subject is poor, whereas the absence of IMP3 in the cancerous tissue of the subject indicates that the prognosis of the subject is good. A method may also comprise determining the level of expression of IMP3 in a cancerous tumor of a subject, wherein a higher level of expression of IMP3 in the cancerous tissue of the subject relative to a control value, e.g., level in a control, indicates that the prognosis of the subject is poor, whereas a lower or similar level of expression of IMP3 in the cancerous tissue of the subject relative to that in the control indicates that the prognosis of the subject is good. A poor prognosis indicates that the cancer is of an aggressive or invasive type, likely to progress fast and/or likely to metastasize.

IMP3 is an oncofetal protein and is a member of the insulin-like growth factor II (IGF-II) mRNA binding protein (IMP) family that consists of IMP1, IMP2 and IMP3[11]. IMP family members play an important role in RNA trafficking and stabilization, cell growth, and cell migration during the early stages of embryogenesis[12]. The IMP3 gene is located on chromosome $7p11.2 \pm 11$ cM[13] and is identical to the KOC (KH domain containing protein overexpressed in cancer) protein that was originally cloned from a pancreatic tumor cDNA screen[14]. IMP3 is expressed in developing epithelium, muscle and placenta during early stages of human and mouse embryogenesis, but it is expressed at low or undetectable levels in adult tissues[11,12]. The amino acid sequence of the human IMP3 protein is set forth in GenBank Accession Nos. AAC35208 and NP_006538.2 and is encoded by the nucleotide sequence set forth in GenBank Accession Nos. U97188 and NM_006547.2. The protein has several RNA recognition motifs and K homology RNA-binding domains, type I (see GenBank entries). The nucleotide and amino acid sequences of the human IMP3 protein are set forth below:

(SEQ ID NO: 1)
```
atgaacaaactgtatatcggaaacctcagcgagaacgccgcccctcggacctagaaagtatcttcaaggacgccaagatcccggtg tcgggacccttcctggtgaagactggctacgcgttcgtggactgcccggacgagagctgggccctcaaggccatcgaggcgctttca ggtaaaatagaactgcacgggaaacccatagaagttgagcactcggtcccaaaaaggcaaaggattcggaaacttcagatacgaaat atcccgcctcatttacagtgggaggtgctggatagtttactagtccagtatggagtggtggagagctgtgagcaagtgaacactgactc ggaaactgcagttgtaaatgtaacctattccagtaaggaccaagctagacaagcactagacaaactgaatggatttcagttagagaattt caccttgaaagtagcctatatccctgatgaaatggccgcccagcaaaacccttgcagcagccccgaggtcgccggggcttggc agaggggctcctcaaggcaggggtctccaggatccgtatccaagcagaaaccatgtgatttgcctctgcgcctgctggttcccaccca atttgttggagccatcataggaaaagaaggtgccaccattcggaacatcaccaaacagacccagtctaaaatcgatgtccaccgtaaa gaaaatgcgggggctgctgagaagtcgattactatcctctctactcctgaaggcacctctgcggcttgtaagtctattctggagattatgc ataaggaagctcaagatataaaattcacagaagagatccccttgaagatttttagctcataataactttgttggacgtcttattggtaaagaa ggaagaaatcttaaaaaaattgagcaagacacagacactaaaatcacgatatctccattgcaggaattgacgctgtataatccagaacg cactattacagttaaaggcaatgttgagacatgtgccaaagctgaggaggagatcatgaagaaaatcagggagtcttatgaaaatgata ttgcttctatgaatcttcaagcacatttaattcctggattaaatctgaacgccttgggtctgttcccacccacttcagggatgccacctccca cctcagggccccttcagccatgactcctccctacccgcagtttgagcaatcagaaacggagactgttcatctgtttatcccagctctatc agtcggtgccatcatcggcaagcagggccagcacatcaagcagctttctcgctttgctggagcttcaattaagattgctccagcgaa gcaccagatgctaaagtgaggatggtgattatcactggaccaccagaggctcagttcaaggctcagggaagaatttatggaaaaatta aagaagaaactttgttagtcctaaagaagaggtgaaacttgaagctcatatcagagtgccatcctttgctgctggcagagttattggaa aaggaggcaaaacggtgaatgaacttcagaatttgtcaagtgcagaagttgttgtccctcgtgaccagacacctgatgagaatgacca agtggttgtcaaaataactggtcacttctatgcttgccaggttgcccagagaaaaattcaggaaattctgactcaggtaaagcagcacca acaacagaaggctctgcaaagtggaccacctcagtcaagacggaagtaa
```

-continued (SEQ ID NO: 2)

```
MNKLYIGNLSENAAPSDLESIFKDAKIPVSGPFLVKTGYAFVDCPDESWALKAIEALS

GKIELHGKPIEVEHSVPKRQRIRKLQIRNIPPHLQWEVLDSLLVQYGVVESCEQVNTD

SETAVVNVTYSSKDQARQALDKLNGFQLENFTLKVAYIPDEMAAQQNPLQQPRGRR

GLGQRGSSRQGSPGSVSKQKPCDLPLRLLVPTQFVGAIIGKEGATIRNITKQTQSKIDV

HRKENAGAAEKSITILSTPEGTSAACKSILEIMHKEAQDIKFTEEIPLKILAHNNFVGRL

IGKEGRNLKKIEQDTDTKITISPLQELTLYNPERTITVKGNVETCAKAEEEIMKKIRES

YENDIASMNLQAHLIPGLNLNALGLFPPTSGMPPPTSGPPSAMTPPYPQFEQSETETV

HLFIPALSVGAIIGKQGQHIKQLSRFAGASIKIAPAEAPDAKVRMVIITGPPEAQFKAQ

GRIYGKIKEENFVSPKEEVKLEAHIRVPSFAAGRVIGKGGKTVNELQNLSSAEVVVPR

DQTPDENDQVVVKITGHFYACQVAQRKIQEILTQVKQHQQQKALQSGPPQSRRK
```

Determining the presence or the level of IMP3 (or expression of IMP3) in a cell or a biological sample includes determining qualitatively or quantitatively the presence of IMP3 protein or degradation product thereof, the presence of IMP3 mRNA or pre-mRNA, or the presence of any biological molecule or product that is indicative of IMP3 expression, or degradation product thereof. The level of IMP3 may also be determined by detecting and/or measuring the level of IMP3 autoantibodies.

It may be sufficient to detect the presence of IMP3 rather than determining its level and comparing it to a standard or control level, as IMP3 levels are relatively low in normal cells and tissues and may not be detectable by the usual methods of detection, e.g., immunohistochemistry. However, when comparing an IMP3 level to a control level, a control may be a value that corresponds to the level of IMP3 in a normal or healthy tissue of the same type as that from which a sample was obtained. A control may also be an average or mean value of at least 2, 5, 10 or more values of levels of IMP3 in normal or healthy tissues. A control may also be a normal control sample, i.e., a sample obtained from a normal or healthy individual, or an individual that does not have cancer, or at least not the type of cancer that is being investigated. A control may also be a value obtained from non-cancerous tissue that is adjacent to the cancerous tissue from which a value was obtained.

In one embodiment, a value obtained from a subject is compared to other values, e.g., control values, present in computer readable form. For example, a value obtained from a subject may be entered into an algorithm or software program comprising one or more values, e.g., control values, and values from cancerous specimens, and a comparison is effected by the software program. A software program may also provide a conclusion based on the comparison, e.g., likelihood of cancer progression or metastasis.

For purposes of comparison, a test sample and normal control sample may be of the same type, that is, obtained from the same biological source. A normal control sample can also be a standard sample that contains the same concentration of IMP3 that is normally found in a biological sample of the same type and that is obtained from a healthy individual, e.g., an individual who does not have cancer. For example, there can be a standard normal control sample for the amounts of IMP3 normally found in a cell or tissue.

When comparing an IMP3 level to a control value, a poor prognosis may be concluded from the presence of at least about 50%, 2 fold, 5 fold, 10 fold, 30 fold, 50 fold, 100 fold or more IMP3 in the sample of the subject compared to the control value. The term "higher level" in the context of levels of IMP3 in a sample from a patient relative to a control value of the level in a tissue from a healthy subject refers to a level that is statistically significant or significantly above levels found in the control value or tissue from the healthy subject. The term "statistically significant" or "significantly" refers to statistical significance and generally means a two standard deviation (2SD) above normal, or higher, concentration of the marker. The levels of IMP3 can be represented by arbitrary units, for example as units obtained from a densitometer, luminometer, or an ELISA plate reader. Ratios or differences in number of units from a cancerous sample and number of units from a control sample, e.g., an adjacent non-cancerous tissue, may be used to determine the prognosis of the patient from whom the samples were taken. These ratios and differences are further discussed herein in the context of particular methods of detection of IMP3 mRNA or protein.

Generally, the presence or amount of IMP3 will be determined in a sample obtained from a tumor. However, it may also be possible that high IMP3 levels located on cells other than the tumor cells (e.g., red or white blood cells) is indicative of a bad prognosis of a cancer, in which case one could determine IMP3 presence or levels in these other cells. A control value or sample would then be obtained from the same type of cells.

A sample may be obtained from a primary tumor. Alternatively, it may also be obtained from a metastatic tumor. A sample may be obtained from a surgically removed tumor, e.g., from a kidney tumor. In one embodiment, a sample is obtained from tissue removed in a radical or partial nephrectomy. When a nephrectomy is performed, IMP3 levels may be measured in cancerous tissue as well as in non-cancerous tissue of the kidney. Similarly, when a tissue or organ is removed for treating another type of cancer, a cancerous sample and a control sample may be obtained from the same tissue or organ.

The level of IMP3 may be determined directly in a biological specimen, e.g., a biopsy, obtained from a subject. Depending on the method used to determine the level of IMP3, it may be desirable to treat a biological specimen prior to measuring the level of IMP3. For example, one or more cells may be isolated from the biological specimen. Fractions of the specimen may be prepared. In other cases, proteins or specific proteins may be isolated or purified from of the sample. In other cases, nucleic acids, e.g., RNA may be isolated or purified from of the sample. For example, in a case when IMP3 protein is detected or measured, one may wish to isolate proteins from the sample, and one may even want to isolate IMP3 proteins from most of the other proteins. When IMP3 mRNA is detected or measured, one may want to isolate total RNA from the sample, and optionally isolate and/or amplify IMP3 mRNA.

The methods described herein are useful for predicting the prognosis of subjects having any one of a variety of cancers. For example, the cancer can be kidney cancer, e.g., renal cell carcinoma (RCC). RCC embraces a group of renal cancers, all of which are derived from the renal tubular epithelium but each with distinct clinical, pathologic, and genotypic features. Examples of RCC include clear cell RCC, papillary RCC, chromophobe RCC, and collecting duct carcinoma. The RCC may be a stage I, II, III or IV. Stages I-III (T3, N0, M0) tumors define localized RCC, whereas most of stage IV tumors defines metastasized RCC.

Other cancers include urogenital cancer, e.g., urothelial carcinomas in urinary bladder, kidney, pelvic and ureter. An examply bladder carcinoma is urothelial carcinoma of the bladder. The majority (75%) of these carcinomas are early stages (i.e., stage Ta and T1) of superficial urothelial carcinomas and can be prognosed and diagnosed as described herein. Generally, the following other tumors or carcinomas of the bladder can also be prognosed and diagnosed as described herein: urothelial (transitional cell) carcinoma, including noninvasive urothelial tumors, invasive urothelial tumors, superficial urothelial tumors, papillary urothelial tumors (invasive or non invasive), papillomas, papillary urothelial neoplasms of low malignant potential, papillary urothelial carcinoma (low grade or high grade), flat urothelial tumors, noninvasive flat urothelial carcinomas, flat carcinoma in situ (cis), and flat invasive urothelial carcinomas.

Other cancers whose development may potentially be prognosticated as described herein include melanoma, prostate carcinoma, lung carcinomas (non-small cell carcinoma, small cell carcinoma, neuroendocrine carcinoma and carcinoid tumor), breast carcinomas (ductal carcinoma, lobular carcinoma and mixed ductal and lobular carcinoma), thyroid carcinomas (papillary thyroid carcinoma, follicular carcinoma and medullary carcinoma), brain cancers (meningioma, astrocytoma, glioblastoma, cerebellum tumors, medulloblastoma, ependymoma), pancreatic carcinoma, ovarian carcinomas (serous, mucinous and endometrioid types), cervical cancers (squamous cell carcinoma in situ, invasive squamous cell carcinoma and endocervical adenocarcinoma), uterine endometrial carcinoma (endometrioid, serous and mucinous types), primary peritoneal carcinoma, mesothelioma (pleura and peritoneum), eye cancer (retinoblastoma), muscle (rhabdosarcoma and leiomyosarcoma), lymphomas, esophageal cancer (adenocarcinoma and squamous cell carcinoma), gastric cancers (gastric adenocarcinoma and gastrointestinal stroma tumor), liver cancers (hepatocellular carcinoma and bile duct cancer), small intestinal tumors (small intestinal stromal tumor and carcinoid tumor) colon cancer (adenocarcinoma of the colon, colon high grade dysplasia and colon carcinoid tumor), and adrenal carcinoma.

Based at least on the observation that certain primary tumors have a high IMP3 level (see Examples), determining the presence or levels of IMP3 in a subject or a biological sample may also be used to determine whether a subject has or is likely to develop cancer (diagnostic method). In one embodiment, a method for determining whether a subject has or is likely to develop cancer comprises determining the presence of IMP3 in the subject, such as in cells or tissues of the subject. The method allows the detection or likelihood of development of any cancer that is associated with high IMP3 expression, as further described herein. A method may involve measuring levels of IMP3 in a test sample obtained from a patient having or suspected of having cancer. A method may further comprise comparing the observed levels of IMP3 to a control or to levels of IMP3 found in a normal control sample, for example a sample obtained from a subject that does not have cancer. The presence of IMP3 or the presence of IMP3 at levels that are higher than levels that are observed in the normal control indicate the presence of cancer or the likelyhood of developing cancer. Exemplary cancers include kidney cancer, such as RCC, and urothelial cancers, e.g., superficial urothelial carcinoma of the bladder.

Additionally, disease progression can be assessed by following IMP3 levels in individual patients over time. Accordingly, methods provided herein also include methods for monitoring the progression of cancer in a subject, comprising, e.g., monitoring the presence or level of IMP3 in a cell, e.g., in a cancerous cell or tumor, of the subject over time. An increase of IMP3 in cancer cells, e.g., over time, indicates that the cancer is progressing. In another embodiment, a reference reading is taken after surgical removal of tissue, e.g., cancerous tissue, then another taken at regular intervals. Any rise in IMP3 levels could be indicative of a relapse, or possibly metastasis.

The information provided by the methods described herein may be used by the physician in determining the most effective course of treatment. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer progression or metastasis is likely, it can be advantageous to precede or follow surgical treatment with chemotherapy, radiation, immunotherapy, biological modifier therapy, gene therapy, vaccines, and the like, or adjust the span of time during which the patient is treated.

Also provided herein are methods for treating a subject having cancer. A method may comprise (i) determining the presence or level of IMP3 in a cancerous tumor of a subject; and (ii) if IMP3 is present or is present at a higher level in the cancerous tumor of the subject relative to a control, treating the subject aggressively, whereas if no IMP3 is detected or if the level of IMP3 in the cancerous tumor of a subject is statistically within the range of a control, treating the subject less aggressively. An aggressive therapy may comprise surgical removal of cancer cells or a tissue comprising the cancer cells, e.g., nephrectomy in the case of kidney cancer, chemotherapy, radiation, or a combination thereof. Surgical removal may be followed by early systematic therapy. The treatment may then be followed by monitoring of IMP3 levels.

In one embodiment, a partial or radical nephrectomy or cancer tissue resection is conducted in a subject having a kidney cancer, e.g., RCC, and the presence or level of IMP3 is determined in the tissue, e.g., tumor tissue obtained by the nephrectomy. If IMP3 is detected in the cancerous tissue, the subject is then treated aggressively, e.g., with postoperative adjuvant therapy, such as with anti-angiogenic agents and/or other drugs, e.g., Nexavar® (sorafenib) and Sutent® (sunitinib). If IMP3 is not detected in the cancerous tissue, then the subject may be spared postoperative adjuvant therapy or other aggressive treatment.

IMP3 status in cancer patients, such as in RCC, can be added in the pathology report with other pathological predictors including tumor size, grade, subtype, and stage for the patient's outcome information and clinical treatment.

In one embodiment, measuring the presence or level of IMP3 is combined with the determination of another prognostic factor, such that the combined determination results in a more accurate prognosis then determining either prognostic factor alone. Other prognostic factors that may be determined include tumor stage, size, grade, necrosis, histology type (clear cell, papillary and chromophobe types) and Eastern Cooperative Oncology Group (ECOG) performance status, and the tumor-node-metastasis (TNM) staging system. In a preferred embodiment, a prognostic method comprises determining the presence or level of IMP3 and determining the stage of the tumor. As described in the Examples, the combination of these two prognostic factors provides much better prognostic information compared with TNM stage alone. For example, the stage and IMP3 level may be compared to the data set forth in the diagram in FIG. 9. This diagram provides that the best to worst diagnosis are as follows (starting from best to worst): stage 1 and 2 RCC with negative IMP3; stage 3 RCC with negative IMP3; stage 1 RCC with low positive IMP3 and all stage RCC with high positive IMP3 and stage 2 and 3 RCC with low positive IMP3. The meaning of "low positive" and "high positive" IMP3 levels is provided in the Examples.

In addition, other prognostic factors for renal cancer, e.g., RCC, which may be combined with IMP3 presence of levels include Von Hippel-Linau gene alteration, DNA ploidy, and the following biomarkers: carbonic anhydrase IX (CAIX or CA9), adipose differentiation-related protein (ADFP), p53, mdm2, p27, cyclin A, cyclin D1, PTEN, Ki-67, proliferating cell nuclear antigen (PCNA); cadherins, catenins, MMP-9, MMP-E2/E-cadherin, CD44, EpCAM, vimentin, MUC1, and immunal regulators (e.g., B7-H1 and B7-H4). These markers are all discussed in Zhong Jiang (2007) Expert Rev. Mol. Diagn. 7:1-15, which is incorporated by reference herein.

Determining the presence or level of IMP3 may also be combined with the detection of one or more other biomarkers for which increased or decreased expression correlates with cancer. The selected biomarker can be a general diagnostic or prognostic marker useful for multiple types of cancer, such as CA 125, CEA or LDH, or can be a cancer-specific diagnostic or prognostic marker, such as a colon cancer marker (for example, sialosyl-TnCEA, CA19-9, or LASA), breast cancer marker (for example, CA 15-2. Her-2/neu and CA 27.29), ovarian cancer marker (for example, CA72-4), lung cancer (for example, neuron-specific enolase (NSE) and tissue polypeptide antigen (TPA)), prostate cancer (for example, PSA, prostate-specific membrane antigen and prostatic acid phosphatase), melanoma (for example, S-100 and TA-90), as well as other biomarkers specific for other types of cancer. Those skilled in the art will be able to select useful diagnostic or prognostic markers for detection in combination with IMP3. Similarly, three or more, four or more or five or more or a multitude of biomarkers can be used together for determining a diagnosis or prognosis of a patient.

Also provided herein are kits, e.g., kits for determining the presence or level of IMP3 in a subject or in a biological sample of a subject. A kit may comprise any agent useful for qualitatively or quantitatively detecting IMP3 proteins or mRNA (including potentially pre-mRNA), such as agents further described herein. A kit may further comprise a control, such as a control value or control sample or control tissue. A control may be protein or RNA attached to a solid support. A kit may also comprise additional components or reagents necessary for the detection of IMP3, such as secondary antibodies for use in immunohistochemistry. A kit may further comprise one or more other biomarkers or reagents for evaluating other prognostic factors, e.g., tumor stage.

IMP3 Protein Detection Techniques

Methods for the detection of protein, e.g., IMP3 protein, are well known to those skilled in the art, and include ELISA (enzyme linked immunosorbent assay), RIA (radioimmunoassay), Western blotting, and immunohistochemistry. Immunoassays such as ELISA or RIA, which can be extremely rapid, are more generally preferred. These methods use antibodies, or antibody equivalents, to detect IMP3 protein. Antibody arrays or protein chips can also be employed, see for example U.S. Patent Application Nos: 20030013208A1; 20020155493A1, 20030017515 and U.S. Pat. Nos. 6,329,209; 6,365,418, herein incorporated by reference in their entirety.

ELISA and RIA procedures may be conducted such that a IMP3 standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, IMP3 in the sample is allowed to react with the corresponding immobilized antibody, radioisotope- or enzyme-labeled anti-IMP3 antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring IMP3 levels comprises the steps of: contacting a biological specimen with an antibody or variant (e.g., fragment) thereof which selectively binds IMP3, and detecting whether said antibody or variant thereof is bound to said sample and thereby measuring the levels of IMP3. A method may further comprise contacting the specimen with a second antibody, e.g., a labeled antibody. The method may further comprise one or more steps of washing, e.g., to remove one or more reagents.

Enzymatic and radiolabeling of IMP3 and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It may be desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect IMP3 according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-IMP3 antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of human IMP3, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy. The results may be quantitated, e.g., as described in the Examples.

As further described in the Examples, immunohistochemical analysis optionally coupled with quantification of the signal may be conducted as follows. IMP3 expression may be directly evaluated in the tissue by preparing immunohistochemically stained slides with, e.g., an avidin-biotinylated peroxidase complex system, as further described in the Examples. Tumor cells with dark brown color indicate high levels of IMP3, whereas cells that do not have a detectable level of IMP3 will not appear brown, but rather blue, e.g., if cells are hematoxycilin stained. Accordingly, a subject, e.g., a pathologist, may determine by merely looking at a slide under a microscope whether cells are brown or not and therefore whether they contain IMP3, the presence of which would be indicative of a poor prognosis.

Evaluation of the presence of brown stain, i.e., IMP3, may also be done by quantitative immunohistochemical investigation, e.g., with a computerized image analyzer (e.g., Automated Cellular Imaging System, ACIS, ChromaVision Medical System Inc., San Juan Capistrano, Calif.) may be used for evaluation of the levels of IMP3 expression in the immunostained tissue samples. Using ACIS, "cytoplasmic staining" may be chosen as program for IMP3 detection. Different areas of immunostained tumor samples may be analyzed with the ACIS system. With ACIS, positive staining may be calculated by applying two thresholds with one recognizing blue background (hematoxylin stained) cells and another recognizing brown positive cells. The integrated optical density (IOD) is the sum of pixels times (multiplied by) the intensity of those pixels. Accordingly, brown IOD is the sum of brown pixels times the intensity of the brown pixels and blue IOD is the sum of blue pixels times the intensity of the blue pixels. ACIS values can be calculated as brown IOD divided by the sum of the blue area and the brown area, i.e., divided by (blue IOD+brown IOD). An average of the ACIS values that is more than 1, e.g., about 1.1, 1.2, 1.3, 1.4, 1.5, 2, 2.5, 3, 5, 10, 30, 100 or more indicates an elevated IMP3 expression and therefore a poor prognosis.

Other machine or autoimaging systems may also be used to measure immunostaining results for IMP3. As used herein, "quantitative" immunohistochemistry refers to an automated method of scanning and scoring samples that have undergone immunohistochemistry, to identify and quantitate the presence of a specified biomarker, such as an antigen or other protein. The score given to the sample is a numerical representation of the intensity of the immunohistochemical staining of the sample, and represents the amount of target biomarker present in the sample. As used herein, Optical Density (OD) is a numerical score that represents intensity of staining. As used herein, semi-quantitative immunohistochemistry refers to scoring of immunohistochemical results by human eye, where a trained operator ranks results numerically (e.g., as 1, 2 or 3).

Various automated sample processing, scanning and analysis systems suitable for use with immunohistochemistry are available in the art. Such systems may include automated staining (see, e.g, the Benchmark™ system, Ventana Medical Systems, Inc.) and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Another method that may be used for detecting and quantitating IMP3 protein levels is Western blotting, e.g., as described in the Examples. Tumor tissues may be frozen and homogenized in lysis buffer. Immunodetection can be performed with an IMP3 antibody using the enhanced chemiluminescence system (e.g., from PerkinElmer Life Sciences, Boston, Mass.). The membrane may then be stripped and re-blotted with a control antibody, e.g., anti-actin (A-2066) polyclonal antibody from Sigma (St. Louis, Mo.). The intensity of the signal may be quantified by densitometry software (e.g., NIH Image 1.61). After quantification of the IMP3 and control signals (e.g., actin), the relative expression levels of IMP3 are normalized by amount of the actin in each lane, i.e., the value of the IMP3 signal is divided by the value of the control signal. IMP3 protein expression is considered to be elevated (and therefore predictive of a poor prognosis) when the value of IMP3/actin is more than 1, e.g., about 1.1, 1.2, 1.3, 1.4, 1.5, 2, 2.5, 3, 5, 10, 30, 100.

Anti-IMP3 antibodies may also be used for imaging purposes, for example, to detect the presence of IMP3 in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In) and technetium ($^{99}$mTc), fluorescent labels, such as fluorescein and rhodamine, and biotin. Immunoenzymatic interactions can be visualized using different enzymes such as peroxidase, alkaline phosphatase, or different chromogens such as DAB, AEC or Fast Red.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the patient, such as barium or caesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99 m. The labeled antibody or antibody fragment will then preferentially accumulate at the location of cells which contain IMP3. The labeled antibody or variant thereof, e.g., antibody fragment, can then be detected using known techniques.

Antibodies that may be used to detect IMP3 include any antibody, whether natural or synthetic, full length or a fragment thereof, monoclonal or polyclonal, that binds sufficiently strongly and specifically to the IMP3 to be detected, e.g., human IMP3. An antibody may have a Kd of at most about $10^{-6}$M, $10^{-7}$M, $10^{-8}$M, $10^{-9}$M, $10^{-10}$ M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to IMP3 relative to other proteins, such as related proteins, e.g., IMP1 and IMP2.

Antibodies are commercially available, e.g., from DAKO (L523S) or may be prepared according to methods known in the art.

Antibodies and derivatives thereof that may be used encompasses polyclonal or monoclonal antibodies, chimeric, human, humanized, primatized (CDR-grafted), veneered or single-chain antibodies, phase produced antibodies (e.g., from phage display libraries), as well as functional, i.e., IMP3 binding fragments, of antibodies. For example, antibody fragments capable of binding to IMP3 or portions thereof, including, but not limited to Fv, Fab, Fab' and F(ab')$_2$ fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies.

In some embodiments, agents that specifically bind to IMP3 other than antibodies are used, such as peptides. Peptides that specifically bind to IMP3 can be identified by any means known in the art. For example, specific peptide binders of IMP3 can be screened for using peptide phage display libraries.

Generally, an agent that is capable of detecting an IMP3 polypeptide, such that the presence of IMP3 is detected and/or quantitated, may be used. As defined herein, an "agent" refers to a substance that is capable of identifying or detecting IMP3 in a biological sample (e.g., identifies or detects IMP3 mRNA, IMP3 DNA, IMP3 protein). In one embodiment, the agent is a labeled or labelable antibody which specifically binds to IMP3 polypeptide. As used herein, the phrase "labeled or labelable" refers to the attaching or including of a label (e.g., a marker or indicator) or ability to attach or include a label (e.g., a marker or indicator). Markers or indicators include, but are not limited to, for example, radioactive molecules, colorimetric molecules, and enzymatic molecules which produce detectable changes in a substrate.

In addition, an IMP3 protein may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modem laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 (Hutchens & Yip) and WO 98/59361 (Hutchens & Yip). The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to be mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to better quantify the amount of the biomolecule present in the first sample. In certain embodiments, the identity of the biomolecules in the first and second sample can also be determined.

IMP3 RNA Detection Techniques

Any method for qualitatively or quantitatively detecting IMP3 RNA, e.g., mRNA, may be used.

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994).

In one embodiment, quantitative real-time polymerase chain reaction (qRT-PCR) is used to evaluate mRNA levels of IMP3 (see Examples). IMP3 and a control mRNA, e.g., glyceraldehyde-3-phosphate dehydrogenase (GAPDH) mRNA levels may be quantitated in cancer tissue and adjacent benign tissues. For this, frozen tissues may be cut into 5 micron sections and total RNA may be extracted, e.g., by Qiagen RNeasy Mini Kit (Qiagen, Inc., Valencia, Calif.). A certain amount of RNA, e.g., five hundred nanograms of total RNA, from each tissue may be reversely transcribed by using, e.g., Qiagen Omniscript RT Kit. Two-step qRT-PCR may be performed, e.g., with the ABI TaqMan PCR reagent kit (ABI Inc, Foster City, Calif.), and IMP3 primers and GAPDH primers, and the probes for both genes on ABI Prism 7700 system. The primers that may be used are set forth in the Examples. The IMP3 copy number may then be divided by the GAPDH copy number and multiplied by 1,000 to give a value for the particular subject. In other words, the amount of IMP3 mRNA was normalized with the amount of GAPDH mRNA measured in the same RNA extraction to obtain an IMP3/GAPDH ratio. A ratio that is equal to or more than 1, e.g., about 1.1, 1.2, 1.3, 1.4, 1.5, 2, 2.5, 3, 5, 10, 30, 100 may be considered as a high IMP3 expression and therefore a poor prognosis.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO9322461.

Primers that may be used for amplification of IMP3 nucleic acid portions are set forth in the Examples.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

Another method for evaluation of IMP3 expression is to detect gene amplification by fluorescent in situ hybridization (FISH). FISH is a technique that can directly identify a specific region of DNA or RNA in a cell and therefore enables to visual determination of the IMP3 expression in tissue samples. The FISH method has the advantages of a more objective scoring system and the presence of a built-in internal control consisting of the IMP3 gene signals present in all non-neoplastic cells in the same sample. Fluorescence in situ hybridization is a direct in situ technique that is relatively rapid and sensitive. FISH test also can be automated. Immunohistochemistry can be combined with a FISH method when the expression level of IMP3 is difficult to determine by immunohistochemistry alone.

Alternatively, mRNA expression can be detected on a DNA array, chip or a microarray. Oligonucleotides corresponding to the IMP3 are immobilized on a chip which is then hybridized with labeled nucleic acids of a test sample obtained from a patient. Positive hybridization signal is obtained with the sample containing IMP3 transcripts. Methods of preparing DNA arrays and their use are well known in the art. (See, for example U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescent-labeled cDNA probes are generated. The microarrays capable of hybridizing to IMP3 cDNA are then probed with the labeled cDNA probes, the slides scanned and fluorescence intensity measured. This intensity correlates with the hybridization intensity and expression levels.

Types of probes for detection of IMP3 RNA include cDNA, riboprobes, synthetic oligonucleotides and genomic probes. The type of probe used will generally be dictated by the particular situation, such as riboprobes for in situ hybridization, and cDNA for Northern blotting, for example. Most preferably, the probe is directed to nucleotide regions unique to IMP3 RNA. The probes may be as short as is required to differentially recognize IMP3 mRNA transcripts, and may be as short as, for example, 15 bases; however, probes of at least 17 bases, more preferably 18 bases and still more preferably 20 bases are preferred. Preferably, the primers and probes hybridize specifically under stringent conditions to a DNA fragment having the nucleotide sequence corresponding to the IMP3 gene. As herein used, the term "stringent conditions" means hybridization will occur only if there is at least 95% and preferably at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

IMP3 Autoantibody Detection

In one embodiment, the level of IMP3 in a subject is determined by the level of IMP3 autoantibodies. An exemplary method comprises determining the presence of IMP3 autoantibodies in a subject, such as in a bodily fluid or sample of the subject, wherein the presence of IMP3 autoantibodies in the bodily fluid or sample of the subject, indicates that the subject has a poor prognosis. In another embodiment, the method comprises determining the level of IMP3 autoantibodies in a subject; comparing the level of autoantibodies to that in a control, e.g., a subject who does not have a cancer, and optionally to that of one or more subjects who have a cancer, e.g., a slow progressive cancer or an invasive cancer and/or a cancer having a high likelihood of metastasis; and or a poor or a good prognosis. A higher level of IMP3 autoantibodies may be a level that is statistically significant, e.g., at least about 1.1, 1.2, 1.3, 1.4, 1.5, 2, 2.5, 3, 5, 10, 30, 100 times higher.

Human tumors stimulate the production of autoantibodies against autologous cellular proteins called tumor associated antigens (TAAs) (see, e.g., Wang et al. New England J. Med. (2005) 353:1224 and Int. J. Oncol. (2005) 26:311). The level of IMP3 autoantibodies may be detected and/or measured in a bodily fluid of a subject, e.g., in blood or serum. Antibodies may be detected by spectrometry, ELISA, PCR, cDNA, peptide phage display, autoantigen microarray, immunoblotting (see, e.g., Casiano et al. (May 2006) Mol. Cell Proteomics). In one embodiment, an IMP3 protein or one or more peptide thereof is used as an agent to detect IMP3 antibodies.

Therapeutic Applications Using IMP3

Based at least on the observation that high IMP3 levels in primary tumors is associated with a higher likelihood of metastasis and a poor prognosis, it may be possible to prevent the likelihood of metastasis and progression of the cancer or prevent cancer altogether by inhibiting or reducing the expression level of IMP3 or IMP3 activity in the tumor or tissue of the subject. In particular, recent studies have demonstrated that IMP3 promotes tumor cell proliferation and invasion (Liao et al. (2006) J. Biol. Chem. 280:18517 and Vikesaa et al. (2006) EMBO J. 25:1456). In one embodiment, a method for treating or preventing cancer, such as kidney or a urogenital cancer, comprises reducing the level of expression of IMP3, reducing the amount of IMP3 protein, or inhibiting the activity of an IMP3 protein. In a method for treatment of cancer, one may reduce IMP3 levels or activity in a tumor, e.g., a primary tumor. In a method for preventing cancer, one may reduce IMP3 levels or activity in tissue likely to develop cancer, e.g., tissue that exhibits high levels of IMP3 expression.

Prophylaxis may be appropriate even at very early stages of the disease, to prevent metastasis. Thus, administration of an agent that reduces IMP3 levels or activity may be effected as soon as cancer is diagnosed, and treatment continued for as long as is necessary, preferably until the threat of the disease has been removed. Such treatment may also be used prophylactically in individuals at high risk for development of certain cancers, e.g., prostate or breast.

RNAi Technology

In one embodiment, IMP3 levels are decreased by administration of or expression in a subject, e.g., in cells or a tissue of the subject, of one or more IMP3 siRNAs.

The term "short interfering RNAs (siRNA)" as used herein is intended to refer to any nucleic acid molecule capable of mediating RNAi or gene silencing. The term siRNA is intended to encompass various naturally generated or synthetic compounds, with RNAi function. Such compounds include, without limitation, duplex synthetic oligonucleotides, of about 21 to 23 base pairs with terminal overlaps of 2 or 3 base pairs; hairpin structures of one oligonucleotide chain with sense and complementary, hybridizing, segments of 21-23 base pairs joined by a loop of, e.g., 3-5 base pairs; and various genetic constructs leading to the expression of the preceding structures or functional equivalents. Such genetic constructs are usually prepared in vitro and introduced in the test system, but can also include siRNA from naturally occurring siRNA precursors coded by the genome of the host cell or animal.

It is not a requirement that the siRNA be comprised solely of RNA. In one embodiment, the siRNA comprises one or more chemical modifications and/or nucleotide analogues. The modification and/or analogue may be any modification and/or analogue, respectively, that does not negatively affect the ability of the siRNA to inhibit IMP3 expression. The inclusion of one or more chemical modifications and/or nucleotide analogues in an siRNA may be preferred to prevent or slow nuclease digestion, and in turn, create a more stable siRNA for practical use. Chemical modifications and/or nucleotide analogues which stabilize RNA are known in the art. Phosphorothioate derivatives, which include the replacement of non-bridging phosphoroyl oxygen atoms with sulfur atoms, are one example of analogues showing increased resistance to nuclease digestion. Sites of the siRNA which may be targeted for chemical modification include the loop region of a hairpin structure, the 5' and 3' ends of a hairpin structure (e.g. cap structures), the 3' overhang regions of a double-stranded linear siRNA, the 5' or 3' ends of the sense strand and/or antisense strand of a linear siRNA, and one or more nucleotides of the sense and/or antisense strand.

As used herein, the term siRNA is intended to be equivalent to any term in the art defined as a molecule capable of mediating sequence-specific RNAi. Such equivalents include, for example, double-stranded RNA (dsRNA), micro-RNA (mRNA), short hairpin RNA (shRNA), short interfering oligonucleotide, and post-transcriptional gene silencing RNA (ptgsRNA).

siRNAs may be introduced into cells to suppress gene expression for therapeutic or prophylactic purposes as described in International Publication Number WO 0175164. Publications describing RNAi technology include but are not limited to the following: U.S. Pat. No. 6,686,463, U.S. Pat. No. 6,673,611, U.S. Pat. No. 6,623,962, U.S. Pat. No. 6,506, 559, U.S. Pat. No. 6,573,099, and U.S. Pat. No. 6,531,644; U.S. publication Nos: 20030153519, 20030167490, International Publication Numbers WO04061081; WO04052093; WO04048596; WO04048594; WO04048581; WO04048566; WO04046320; WO04044537; WO04043406; WO04033620; WO04030660; WO04028471; WO 0175164. Papers which describe the methods and concepts for the optimal use of these compounds include but are not limited to the following: Brummelkamp Science 296: 550-553 (2002); Caplen Expert Opin. Biol. Ther. 3:575-86 (2003); Brummelkamp, Sciencexpress 21 Mar. 3 1-6 (2003); Yu Proc Natl Acad Sci USA 99:6047-52 (2002); Paul Nature Biotechnology 29:505-8 (2002); Paddison Proc Natl Acad Sci USA 99:1443-8 (2002); Brummelkamp Nature 424: 797-801 (2003); Brummelkamp, Science 296: -550-3 (2003); Sui Proc Natl Acad Sci USA 99: 5515-20 (2002); Paddison, Genes and Development 16:948-58 (2002).

A composition comprising an siRNA effective to inhibit IMP3 expression may include an RNA duplex comprising a sense sequence of IMP3. In this embodiment, the RNA duplex comprises a first strand comprising a sense sequence of IMP3 and a second strand comprising a reverse complement of the sense sequence of IMP3. In one embodiment the sense sequence of IMP3 comprises of from 10 to 25 nucleotides in length. More preferably, the sense sequence of IMP3 comprises of from 19 to 25 nucleotides in length. Most preferably, the sense sequence of IMP3 comprises of from 21 to 23 nucleotides in length. The sense sequence of IMP3 preferably comprises a sequence of IMP3 containing a translational start site, and may comprise a portion of IMP3 sequence within the first 400 nt of the human IMP3 mRNA.

In another embodiment, a composition comprising an siRNA effective to inhibit IMP3 expression may comprise in a single molecule a sense sequence of IMP3, the reverse complement of the sense sequence of IMP3, and an intervening sequence enabling duplex formation between the sense and reverse complement sequences. The sense sequence of IMP3 may comprise 10 to 25 nucleotides in length, or more preferably 19 to 25 nucleotides in length, or most preferably 21 to 23 nucleotides in length.

It will be readily apparent to one of skill in the art that an siRNA of the present invention may comprise a sense sequence of IMP3 or the reverse complement of the sense sequence of IMP3 which is less than perfectly complementary to each other or to the targeted region of IMP3. In other words, the siRNA may comprise mismatches or bulges within the sense or reverse complement sequence. In one aspect, the sense sequence or its reverse complement may not be entirely contiguous. The sequence or sequences may comprise one or more substitutions, deletions, and/or insertions. The only requirement of the present invention is that the siRNA sense sequence possess enough complementarity to its reverse complement and to the targeted region of IMP3 to allow for RNAi activity. It is an object of the present invention, therefore, to provide for sequence modifications of an siRNA of the present invention that retain sufficient complementarity to allow for RNAi activity. One of skill in the art may predict that a modified siRNA composition of the present invention will work based on the calculated binding free energy of the modified sequence for the complement sequence and targeted region of IMP3. Calculation of binding free energies for nucleic acids and the effect of such values on strand hybridization is known in the art.

A wide variety of delivery systems are available for use in delivering an siRNA to a target cell in vitro and in vivo. An siRNA of the present invention may be introduced directly or indirectly into a cell in which IMP3 inhibition is desired. An siRNA may be directly introduced into a cell by, for example, injection. As such, it is an object of the invention to provide for a composition comprising an siRNA effective to inhibit IMP3 in injectable, dosage unit form. An siRNA of the present invention may be injected intravenously or subcutaneously as an example, for therapeutical use in conjunction with the methods and compositions of the present invention. Such treatment may include intermittent or continuous administration until therapeutically effective levels are achieved to inhibit IMP3 expression in the desired tissue.

Indirectly, an expressible DNA sequence or sequences encoding the siRNA may be introduced into a cell, and the siRNA thereafter transcribed from the DNA sequence or sequences. It is an object of the present invention, therefore, to provide for compositions comprising a DNA sequence or sequences which encode an siRNA effective to inhibit IMP3 expression.

A DNA composition of the present invention comprises a first DNA sequence which encodes a first RNA sequence comprising a sense sequence of IMP3 and a second DNA sequence which encodes a second RNA sequence comprising the reverse complement of the sense sequence of IMP3. The first and second RNA sequences, when hybridized, form an siRNA duplex capable of forming an RNA-induced silencing complex, the RNA-induced silencing complex being capable of inhibiting IMP3 expression. The first and second DNA sequences may be chemically synthesized or synthesized by PCR using appropriate primers to IMP3. Alternatively, the DNA sequences may be obtained by recombinant manipulation using cloning technology, which is well known in the art. Once obtained, the DNA sequences may be purified, combined, and then introduced into a cell in which IMP3 inhibition is desired. Alternatively, the sequences may be contained in a single vector or separate vectors, and the vector or vectors introduced into the cell in which IMP3 inhibition is desired.

Delivery systems available for use in delivering a DNA composition of the present invention to a target cell include, for example, viral and non-viral systems. Examples of suitable viral systems include, for example, adenoviral vectors, adeno-associated virus, lentivirus, poxvirus, retroviral vectors, vaccinia, herpes simplex virus, HIV, the minute virus of mice, hepatitis B virus and influenza virus. Non-viral delivery systems may also be used, for example using, uncomplexed DNA, DNA-liposome complexes, DNA-protein complexes and DNA-coated gold particles, bacterial vectors such as *salmonella*, and other technologies such as those involving VP22 transport protein, Co-X-gene, and replicon vectors. A viral or non-viral vector in the context of the present invention may express the antigen of interest.

Antisense Technology

In another embodiment, the level of IMP3 is reduced or decreased by administration or the expression of antisense molecules in a subject or tissue or cell thereof.

Gene expression can be controlled through triple-helix formation or antisense DNA or RNA, both of which methods are based on binding of a polynucleotide to DNA or RNA. An antisense nucleic acid molecule which is complementary to a nucleic acid molecule encoding IMP3 can be designed based on the known IMP3 nucleotide sequences. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. A nucleic acid is designed which has a sequence complementary to a sequence of the coding or untranslated region of the shown nucleic acid. Alternatively, an antisense nucleic acid can be designed based upon sequences of the IMP3 gene, which are known or can be identified by screening a genomic DNA library with an isolated nucleic acid of the invention. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1 (1)1986.

In addition, ribozymes can be used to inhibit expression of IMP3. For example, the nucleic acids of the invention can further be used to design ribozymes which are capable of cleaving a single-stranded nucleic acid encoding a IMP3 protein, such as a IMP3 mRNA transcript. A catalytic RNA (ribozyme) having ribonuclease activity can be designed which has specificity for an mRNA encoding IMP3 based upon the sequence of a nucleic acid of the invention. For example, a derivative of a Tetrahymena L-19 IVS RNA can be constructed in which the base sequence of the active site is complementary to the base sequence to be cleaved in a IMP3-encoding mRNA. See for example Cech, et al., U.S. Pat. No. 4,987,071; Cech, et al., U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. Science 261: 1411-1418 (1993). RNA-mediated interference (RNAi) (Fire, et al., Nature 391: 806-811, 1998) may also be used.

IMP3 Blocking Antibodies and Aptamers

In yet another embodiment, IMP3 levels are reduced by administration to or expression in a subject or a cell or tissue thereof, of IMP3 blocking antibodies or aptamers.

Antibodies, or their equivalents and derivatives, e.g., intrabodies, or other IMP3 antagonists may be used in accordance with the present invention for the treatment or prophylaxis of cancers. Administration of a suitable dose of the antibody or the antagonist may serve to block the activity of the protein and this may provide a crucial time window in which to treat the malignant growth.

A method of treatment may involve attachment of a suitable toxin to IMP3 antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of suitable physiologically active compounds, which may be used, for example, to treat cancers.

The antibody (or other inhibitors or intrabody) can be administered by a number of methods. One preferred method is set forth by Marasco and Haseltine in PCT WO94/02610, which is incorporated herein by reference. This method discloses the intracellular delivery of a gene encoding the antibody. One would preferably use a gene encoding a single chain antibody. The antibody would preferably contain a nuclear localization sequence. One preferably uses an SV40 nuclear localization signal. By this method one can intracellularly express an antibody, which can block IMP3 functioning in desired cells.

Where the present invention provides for the administration of, for example, antibodies to a patient, then this may be by any suitable route. If the tumor is still thought to be, or diagnosed as, localized, then an appropriate method of administration may be by injection direct to the site. Administration may also be by injection, including subcutaneous, intramuscular, intravenous and intradermal injections.

Aptamers can be produced using the methodology disclosed in a U.S. Pat. No. 5,270,163 and WO 91/19813.

Other IMP3 Inhibitors

Other agents, e.g., compounds, that inhibit the activity of IMP3 may also be used. Such compounds include small molecules, e.g., molecules that interact with the active site or a binding site of the protein, e.g., an RNA binding site. For example, an IMP3 inhibitory agent may be an agent that inhibits binding of IMP3 to its target mRNA. One agent that can be used is a target RNA or a portion thereof to which IMP3 binds. In one embodiment, a large amount of such an oligonucleotide or nucleic acid is administered to a subject to thereby prevent IMP3 to reach its targets in the cell, and thereby prevent IMP3 activity. An agent may be a portion of IGF-II mRNA to which IMP3 binds, such as a portion of an IGF-II leader 3 mRNA (see, e.g., Nielsen et al. Scand J Clin Lab Invest Suppl. 2001; 234:93). Other agents may be identified according to methods known in the art.

Pharmaceutical Compositions

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters are one preferred mode of administration.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The antibodies, nucleic acids or antagonists of the invention may be administered orally, topically, or by parenteral means, including subcutaneous and intramuscular injection, implantation of sustained release depots, intravenous injection, intranasal administration, and the like. Accordingly, antibodies or nucleic acids of the invention may be administered as a pharmaceutical composition comprising the antibody or nucleic acid of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol Registered TM, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively one may incorporate or encapsulate the compounds in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-Care® (Allergan), Neodecadron® (Merck, Sharp & Dohme), Lacrilube®, and the like, or may employ topical preparations such as that described in U.S. Pat. No. 5,124,155. Further, one may provide an antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The amount of antibody, nucleic acid or inhibitor required to treat any particular disorder will of course vary depending upon the nature and severity of the disorder, the age and condition of the subject, and other factors readily determined by one of ordinary skill in the art.

Immunotherapy

In further aspects, the present invention provides methods for using IMP3 or an immunoreactive polypeptide thereof (or DNA encoding the protein or polypeptides) for immunotherapy of cancer in a patient. Accordingly, IMP3 or an immunoreactive polypeptide thereof may be used to treat cancer or to inhibit the development of cancer.

In accordance with this method, the protein, polypeptide or DNA is generally present within a pharmaceutical composition and/or a vaccine. Pharmaceutical compositions may comprise the full length protein or one or more immunogenic polypeptides, and a physiologically acceptable carrier. The vaccines may comprise the full length protein or one or more immunogenic polypeptides and a non-specific immune response enhancer, such as an adjuvant, biodegradable microsphere (PLG) or a liposome (into which the polypeptide is incorporated).

Alternatively, a pharmaceutical composition or vaccine may contain DNA encoding IMP3 or an immunogenic polypeptide thereof, such that the full length protein or polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus*-Calmette-Guerrin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., PNAS 86:317-321, 1989; Flexner et al., Ann. N.Y Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345, 242; WO 91/02805; Berkner, iotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in published PCT application WO 90/11092, and Ulmer et al., Science 259:1745-1749 (1993), reviewed by Cohen, Science 259: 1691-1692 (1993).

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3-24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against tumor cells, e.g., kidney tumor cells, in a treated patient. A suitable immune response is at least 10-50% above the basal (i.e. untreated) level. In general, the amount of polypeptide present in a dose (or produced in situ by the DNA in a dose)

ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 ml.

IMP3 or an immunogenic polypeptide or immunogenic homolog thereof can be used in cell based immunotherapies, e.g., stimulation of dendritic cells with IMP3 or fusion with IMP3 expressing cells. An "immunogenic homolog" refers to a protein that is at least about 80%, 85%, 90%, 95%, 98% or 99% identical to a wildtype IMP3 protein or a fragment thereof. The modified dendritic cells, once injected into the patient, are a cellular vaccine, where the dendritic cells activate an immune response against the IMP3 expressing cancer.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polyleptic galactide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example. Freund's Incomplete Adjuvant and Complete Adjuvant (Difco Laboratories. Detroit, Mich.) and Merck Adjuvant 65 (Merck and Company, Inc., Rahway, N.J.).

All publications, patents, patent applications, and GenBank Accession numbers mentioned herein are hereby incorporated by reference to the extent necessary to support that for which they have been cited herein. In case of conflict, the present application, including any definitions herein, will control. The present invention is further illustrated by the following examples which should not be construed as limiting in any way. The present invention is further illustrated by the following examples which should not be construed as limiting in any way.

EXAMPLES

Example 1

The RNA-Binding Protein IMP3: a Novel Biomarker to Predict Metastasis and Prognosis of Renal Cell Carcinomas Summary
Background
Distant metastases of renal cell carcinoma (RCC) remain the primary cause of death in patients with this disease and the metastatic potential of localized RCC is often unpredictable. In this study, we investigated whether IMP3, an oncofetal RNA-binding protein, can serve as a biomarker to predict metastasis and prognosis of RCC.

Methods
A total of 501 primary and metastatic RCCs were studied. The 371 patients with localized primary RCCs were further evaluated for survival analysis. The expression of IMP3 in RCC tissues was evaluated by immunohistochemistry and selected cases were also assessed for mRNA and protein expression of IMP3 by quantitative real-time polymerase chain reaction and Western blot analysis.

Findings
The expression of IMP3 was significantly increased not only in the metastatic RCCs but most importantly also in a subset of primary RCCs that were much more likely to subsequently develop metastases. Kaplan-Meier plots and log-rank tests showed that patients without IMP3 expression in their primary localized RCCs had significant longer metastasis-free survival and overall survival than patients with IMP3 expression (P<0.0001). In patients whose localized RCCs were positive for IMP3 versus those with IMP3 negative RCCs, the 5-year metastasis-free survival were 44% vs. 98% [hazards ratio=17.18 (95% confidence interval: 7.82-37.78), stage I], 41% vs. 94% [10.14 (3.46-29.68), stage II] and 16% vs. 62% [4.04 (2.23-7.31), stage III], and the 5-year overall survival rates were 32% vs. 89% [6.44 (3.63-11.42), stage I], 41% vs. 88% [6.93 (2.63-18.27), stage II] and 14% vs. 58% [3.46 (1.98-6.05), stage III] respectively. Multivariate Cox proportional hazards regression analysis showed that the hazard ratio of IMP3 status in primary RCCs were 5.84 (metastasis-free survival, P<0.0001) and 4.01 (overall survival, P<0.0001) respectively, which were much higher than the hazard ratios associated with the other independent risk factors.

Interpretation
IMP3 is an excellent independent prognostic marker that can be used at the time of initial diagnosis of RCC to identify a group of patients with a high potential to develop metastasis and who might benefit from early systemic therapy.

Introduction
Renal cell carcinoma is the most common type of kidney cancer and accounts for about 85 percent of malignant kidney tumors[1,2]. The incidence of renal cell carcinoma has been rising steadily[3]. It is estimated that there will be about 36,160 new cases of kidney cancer in the United States in the year 2005, and about 12,660 people will die from this disease[4].

Surgical resection of primary renal cell carcinoma can be a curative treatment when the disease is localized. However, distant metastasis remains the primary cause of therapeutic failure and cancer death[1,2]. Patients with metastatic disease are typically treated with systemic therapy, which is associated with substantial toxicity[1,2]. Therefore, unless the patient presents with metastatic disease, clinical observation is the standard of care following nephrectomy. Currently, the methods to determine prognosis and select patients for postoperative adjuvant therapy rely mainly on pathological and clinical staging[5-8]. However, as there are remarkable differences in the biological behavior of renal cell carcinomas classified in the same stage, it is very difficult to predict which localized tumor will eventuate in distant metastasis. Approximately twenty percent of patients with localized tumors develop metastasis and the median survival for patients with metastatic disease is approximately 13 months[2,9,10]. Therefore, there is a great need for biomarkers that can accurately distinguish localized tumors with a high probability of metastasis from those that will remain indolent. Using such biomarkers, one can predict the patient's prognosis and can effectively target the individuals who would most likely benefit from adjuvant therapy. Recently, molecular biomarkers are an area of interest for studying renal cell carcinoma.

Various protein markers and gene expression profiles based on DNA microarray analysis have demonstrated potential in predicting disease outcome in renal cell carcinoma[11,12].

IMP3 is a member of the insulin-like growth factor II (IGF-II) mRNA binding protein (IMP) family that consists of IMP1, IMP2 and IMP3[13]. IMP family members play an important role in RNA trafficking and stabilization, cell growth, and cell migration during the early stages of embryogenesis[14]. The IMP3 gene is located on chromosome 7p11.2±11 cM[15] and is identical to the KOC (KH domain containing protein overexpressed in cancer) protein that was originally cloned from a pancreatic tumor cDNA screen[16]. IMP3 is expressed in developing epithelium, muscle and placenta during early stages of human and mouse embryogenesis, but it is expressed at low or undetectable levels in adult tissues[13,14]. The expression of IMP3/KOC is also found in malignant tumors including pancreas, lung, stomach, and colon cancers, and soft tissue sarcomas but it is not detected in adjacent benign tissues[13,16-18]. Moreover, a recent study has demonstrated that IMP3 promotes human leukemia cell proliferation[19]. These findings indicate that IMP3 is an oncofetal protein that may have a critical role in the regulation of cell proliferation. However, the expression of IMP3 in renal cell carcinomas and the relationship between IMP3 and tumor metastasis are unknown. In this study, we investigated whether IMP3 could serve as an independent biomarker to predict metastasis and prognosis in patients with renal cell carcinoma.

Methods

Patients and Tumor Specimens:

Formalin-fixed, paraffin-embedded samples from 406 patients with primary renal cell carcinomas, who underwent radical or partial nephrectomy, were obtained from the archival files at the University of Massachusetts Medical Center (UMMC, n=159), the Massachusetts General Hospital (MGH, n=152) and the City of Hope National Medical Center (CHNMC, n=95). The data from these sources represented all patients for whom archival tissues and adequate clinical follow-up information were readily available. All cases were collected between January of 1989 and December 2003 and the diagnoses were confirmed by at least two pathologists. Staging was based on pathological findings following the American Joint Committee on Cancer (AJCC) staging manual, sixth edition, 2002. Two hundred sixteen patients (pT1a or b) were stage I, 64 patients (pT2) were stage II, 98 patients (pT3a, n=62; pT3b, n=29; pT3, N1, n=7) were stage III and 28 patients (pT2, N2 or M1, n=5; pT3, N2 or M1, n=12; pT4, N2 or M1, n=7; pT4, n=4) were stage IV. Follow-up for this retrospective study was carried out by researchers (ZJ, PGC, and CLW) reviewing the patient clinical records. Metastasis was found in 119 of 406 (29%; UMMC: 27%; MGH: 29%; CHNMC: 34%) patients with primary RCCs during nephrectomy (N=30) or after surgery (N=89). One hundred fifty nine patients out of 406 patients (39%; UMMC: 42%; MGH: 35%; CHNMC: 42%) with primary RCC expired. An additional 95 metastatic renal cell carcinomas (26 of the metastatic RCCs were from the same patients with primary tumors and the others were from the biopsy or resection of metastatic tumors only), which were obtained from lung (n=22), lymph nodes (n=10), gastrointestinal organs including liver, intestines, pancreas, and gallbladder (n=7), bone (n=23), brain (n=8), adrenal, thyroid and ovary (n=10), head and neck area (n=2), soft tissues (n=6), diaphragm, pleura, retroperitoneum and omentum (n=7) at the three institutions, were also examined by immunohistochemistry (IHC) and compared to the primary RCCs. The Institutional Review Board at each institution approved this study.

Immunohistochemical Analysis

Immunohistochemical studies were performed on 5 μm sections of formalin-fixed, paraffin-embedded tissue from nephrectomy specimens by using an avidin-biotinylated peroxidase complex system as a previously published protocol[18] on the DAKO Autostainer (DAKO Corporation, Carpinteria, Calif.). Sections of pancreatic carcinoma with known positivity of IMP3 were used as positive controls for the L523S mouse monoclonal antibody (MAb) specific for IMP3/KOC (Corixa Corporation, Seattle, Wash.) staining Negative controls were performed by replacing the primary antibody with nonimmune IgG. Positive staining of IMP3 was defined as dark brown cytoplasm (FIGS. 1A and B, IMP3 positive), while negative staining of IMP3 was defined as no staining at all (FIG. 1C, IMP3 negative). The status of IMP3 was assessed by a genitourinary pathologist (Z J) without knowledge of the clinical and pathological features of the cases or the clinical outcome. To assess the reproducibility of the immunohistochemical test for IMP3 expression, 50 cases were randomly chosen for independent analysis in terms of positive or negative staining by three other pathologists (C W, P C, and C L). There was complete concurrence of the results by all pathologists. Each positive case was also further evaluated for the percentage of the cells that stained positively and was scored as focal: ≤30%, or diffuse: >30%.

Quantitative Analysis of Immunostaining

A total of 270 different areas (15 different areas per case) from 9 RCC IMP3 positive cases and 9 RCC IMP3 negative cases were quantitatively analyzed by a pathologist (ZJ) using a computerized image analyzer (Automated Cellular Imaging System, ACIS, ChromaVision Medical System Inc., San Juan Capistrano, Calif.) to evaluate the IHC results. With ACIS, positive staining is calculated by applying two thresholds with one recognizing blue background (hematoxylin stained) cells and another recognizing brown positive cells. The integrated optical density (IOD) is that the sum of brown pixels times brown intensity of those pixels. The ACIS values were calculated as IOD was divided by the sum of the blue area and the brown area.

Western Blotting Analysis of IMP3 Expression:

Primary RCC frozen tissues and a metastatic renal cell cancer cell line (ATCC Global Bioresource Center, Manassas, Va., ATCC® Number: HTB-46) were homogenized in 3 volumes of lysis buffer. Immunodetection was performed with IMP3 MAb (L523S) at a 1 ug/ml dilution using the enhanced chemiluminescence system (PerkinElmer Life Sciences, Boston, Mass.). The membrane was stripped and re-blotted with anti-actin (A-2066) polyclonal antibody from Sigma (St. Louis, Mo.). Intensity of the signal was quantified by densitometry software (NIH Image 1.61) and relative expression levels of IMP3 were normalized by amount of the actin in each lane.

Quantitative Real-Time Polymerase Chain Reaction (qRT-PCR)

IMP3 and glyceraldehyde-3-phosphate dehydrogenase (GAPDH, as an internal reference) mRNA levels in RCC tissues were quantified by qRT-PCR. Frozen tissues were cut into 5 micron sections and total RNAs were extracted by Qiagen RNeasy Mini Kit (Qiagen, Inc., Valencia, Calif.). Two-step qRT-PCR was performed with the ABI TaqMan PCR reagent kit (ABI Inc, Foster City, Calif.), and IMP3 primers and GAPDH primers, and the probes for both genes on ABI Prism 7700 system. The primers were used as follow: IMP3 forward primer, 5'-GCT AAA GTG AGG ATG GTG ATT ATC ACT-3' (SEQ ID NO: 3); IMP3 reverse primer, 5'-ACT AAC AAA GTT TTC TTC TTT AAT TTT TCC AT-3' (SEQ ID NO: 4); IMP3 probe, 5' FAM-ACC AGA GGC TCA GTT CAA GGC TCA GGG AA-TAMRA 3' (SEQ ID NO: 5); GAPDH forward primer, 5'-GAAGGTGAAGGTCG-GAGTC-3' (SEQ ID NO: 6); GAPDH reverse primer, 5'-GAAGATGGTGATGGGATTTC-3' (SEQ ID NO: 7); GAPDH probe, 5' FAM-CAAGCTTCCCGTTCTCAGCC-TAMRA 3' (SEQ ID NO: 8). The expression of IMP3 mRNA was normalized with GAPDH mRNA expression measured in the same RNA extraction and calculated as the numbers of IMP3/GAPDH ratio.

Statistical Analysis:

Overall survival was measured from the date of nephrectomy to the date of death or was censored as of the date of the last follow-up visit for survivors. Metastasis-free survival was measured from the date of surgery to the date of first clinical evidence of metastasis, and was censored at the date of death or the date of the last follow-up visit for survivors. The median follow-up was 63 months (range=1-174 months). Age, sex, size of the tumor, tumor stage, grade and histological type, and IMP3 status were collected as baseline variables. The distribution of each baseline variable was compared for IMP3-positive and IMP3-negative subgroups with the Wilcoxon rank sum test for continuous variables and the Fisher's exact test for categorical variables. Thirty-one (stage III: N=7 and Stage IV, N=24) of 406 patients with metastatic disease found during nephrectomy were excluded from the overall and metastasis-free survival study, as the aim of this study was to evaluate the risk of metastases after surgery in patients initially presenting with localized disease. By AJCC TNM staging criteria, most of the stage IV patients (24 of 28, 86%) in this study were found with metastasis (M1: n=13; N2: n=10; N2 and M1: n=1) during surgery. Only four patients with stage IV disease were found without metastasis during nephrectomy and they were excluded from the prognostic analysis, as such a small number of patients would not be informative for the prognostic analysis of patients with stage IV RCCs. Therefore, a total of 371 patients with stage I, II and III disease and without metastasis during surgery were included in our survival analysis. Overall survival and metastasis-free survival of 371 patients were estimated by the Kaplan-Meier method and evaluated with the use of log-rank test for univariate analysis. The Cox proportional-hazard model was used to assess the simultaneous contribution of the following baseline covariates of age, sex, size of the tumor, tumor stage, grade and histological type, and IMP3 status. A two-sided P-value of less than 0.05 was considered to indicate the statistical significance.

Institutional funds supported this study and funding source had no role in making decisions including study design, data collection, analysis, and interpretation, writing of the report, and decision to submit.

Results

Expression of IMP3 in All Primary and Metastatic Renal Cell Carcinomas

Figure 2:
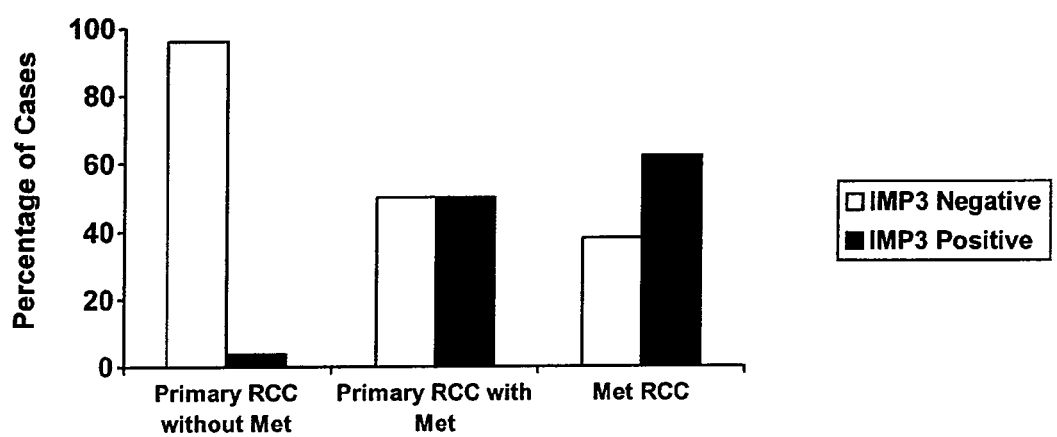
FIG. 2. The percentage of IMP3 expression in patients with primary RCCs without metastasis (Met), primary RCCs with metastasis (Met) and metastatic (Met) RCCs.

IMP3 protein was observed in the cytoplasm of tumor cells (FIGS. 1A and 1B). Expression of IMP3 was found in 62% (59 of 95) of metastatic RCCs, in 50% (60 of 119) of primary RCCs with metastases during and after nephrectomy, and in 4% (11 of 287) metastasis-free primary RCCs (FIG. 2). In 71 positive primary RCCs, the IMP3 positivity was detected in ≤30% tumor cells (focal) in 38 cases, and >30% of tumor cells (diffuse) in 33 cases. No expression of IMP3 was found in benign kidney tissue adjacent to the tumors. The results of quantitative immunohistochemistry showed significant differences in IMP3 staining values between positive and negative cases. The average of the ACIS values was 44.3 in the IMP3 positive RCCs and 0.01 in the IMP3 negative RCCs (P=0.0025).

Figure 3:
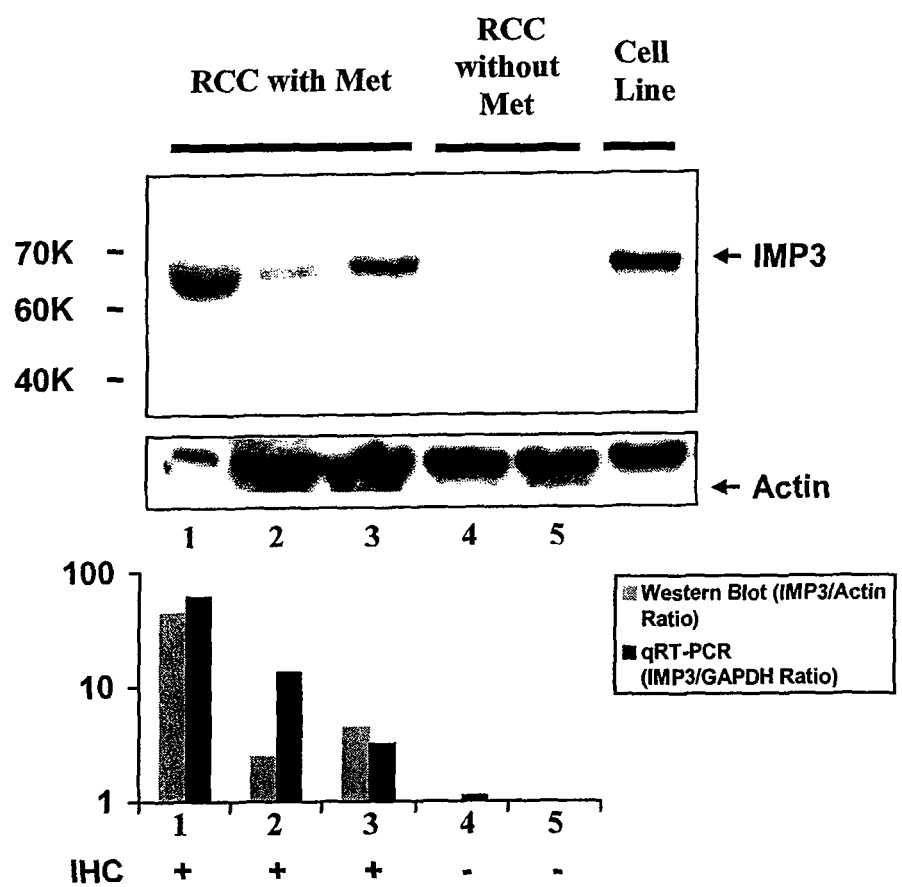
FIG. 3. Western blot analysis of IMP3 expression in primary RCCs. Metastatic RCC cell line (Cell Line) was used for comparison. Actin was included as a loading control. Primary RCCs with Met=primary RCCs with metastasis; RCCs without Met=primary RCCs without metastasis. (Lower) Bar graph showing IMP3 protein levels in above Western blot analysis (case 1-3=RCCs with Met; case 4-5=primary RCCs without Met) and IMP3 mRNA Levels by quantitative real-time PCR analysis in the same sample. A ratio of IMP3 protein expression in Western blot analysis was calculated relative to actin expression and a ratio of IMP3 mRNA expression in quantitative real-time PCR analysis was calculated relative to the housekeeping gene glyceraldehyde-3-phosphate dehydrogenase (GAPDH) expression. IHC=immunohistochemistry; "+"=positive for IMP3 staining by IHC; "−"=negative for IMP3 staining by IHC.

In addition, the reactivity of L523S MAb with IMP3/KOC protein produced by RCCs was determined by Western blot analysis (FIG. 3). L523S MAb reacted with a protein at the expected molecular weight for IMP3 (approximately 65 kilo-dalton). FIG. 3 (upper) showed that IMP3 was highly expressed in the metastatic RCC cell line and three IHC positive cases of primary RCCs with subsequent development of metastasis. In contrast, IMP3 exhibited no expression in two IHC negative cases of primary RCCs without the subsequent development of metastasis.

The over expression of IMP3 mRNA was also detected in primary RCCs. The results of qRT-PCR performed to quantitatively assess the expression levels of IMP3 mRNA in the primary RCCs, which were subject to Western blot analysis, are shown in FIG. 3 (lower). The three IHC positive primary RCCs with subsequent development of metastasis were found to over express IMP3 mRNA as compared to IHC negative primary RCCs without development of metastasis (FIG. 3, lower). Analysis of the agreement between the Western blot test and the real-time PCR analysis of the same samples showed complete agreement between the tests (data not shown). However, since this analysis was based on only five samples, a larger study is needed to show conclusive results.

Characteristics of the Patients

Table 1 provides the relevant clinical characteristics of the 406 patients with primary RCCs. Age was not correlated with the positivity for IMP3 (P=0.28). Male patients were more likely than female patients to show IMP3 expression in their tumors (P=0.015). The expression of IMP3 was strongly associated with standard pathologic predictors of clinical outcome. IMP3 expression was found predominately in large tumors, and tumors with higher grade and stage. Only 10-24% of stage I, II and III RCCs expressed IMP3, whereas 50% of stage IV tumors were positive for IMP3. Expression of IMP3 was found predominately in high-grade (grade 3 and 4) tumors and all grade 1 RCCs were negative for IMP3. The IMP3 positivity rate was slightly increased in conventional (clear cell) type carcinomas (23%) as compared with papillary (11%) and chromophobe (15%) RCCs. Two cases of unclassified RCCs were all positive for IMP3. IMP3 expression in primary RCCs was associated with a significant increase in the risk of death. Ninety percent (64 of 71) of patients with expression of IMP3 died and 28% (95 of 335) of patients without IMP3 expression expired.

TABLE 1

Clinicopathological Characteristics of Renal Cell Carcinoma Patients

| Characteristic | IMP3+ (N = 71) | IMP3− (N = 335) | P Value |
|---|---|---|---|
| Sex: | | | |
| Female | 17 (11%) | 132 (89%) | 0.015 |
| Male | 54 (21%) | 203 (79%) | |
| Age - yr | 61.8 ± 11.2* | 59.5 ± 14.1 | 0.28 |
| Tumor stage | | | |
| I | 22 (10%) | 194 (90%) | <0.0001 |
| II | 11 (17%) | 53 (83%) | |
| III | 24 (24%) | 74 (76%) | |
| IV | 14 (50%) | 14 (50%) | |
| Tumor Size | 8.5 ± 4.9* | 6.1 ± 3.7 | <0.0001 |

TABLE 1-continued

Clinicopathological Characteristics of Renal Cell Carcinoma Patients

| Characteristic | IMP3+ (N = 71) | IMP3− (N = 335) | P Value |
|---|---|---|---|
| Tumor Grade | | | |
| 1 | 0 (0%) | 30 (100%) | <0.0001 |
| 2 | 17 (9%) | 169 (91%) | |
| 3 | 36 (24%) | 111 (76%) | |
| 4 | 18 (42%) | 25 (58%) | |
| Histological types | | | |
| Clear cell type | 58 (23%) | 256 (74%) | 0.04 |
| Papillary | 7 (11%) | 56 (89%) | |
| Chromophobe | 4 (15%) | 23 (85%) | |
| Unclassified | 2 (100%) | 0 (0%) | |

*Plus-minus values are means ± SD.

Expression of IMP3 and Prognosis in Patients with Localized Renal Cell Carcinoma during Nephrectomy A total of 371 patients who did not have metastasis at the time of surgery were included in follow-up analysis. The percentage of metastasis after surgery was significantly different between the IMP3 positive patients and the IMP3 negative patients in their primary RCCs. Eighty percent (43 of 54) of patients with IMP3 positivity in their primary RCCs subsequently developed metastasis (median follow-up=38 months, range=1-155 months), whereas 13% (41 of 317) of patients without expression of IMP3 in their primary tumors were found to have metastases after surgery (median follow-up=70 months, range=1-174 months).

Figure 4:
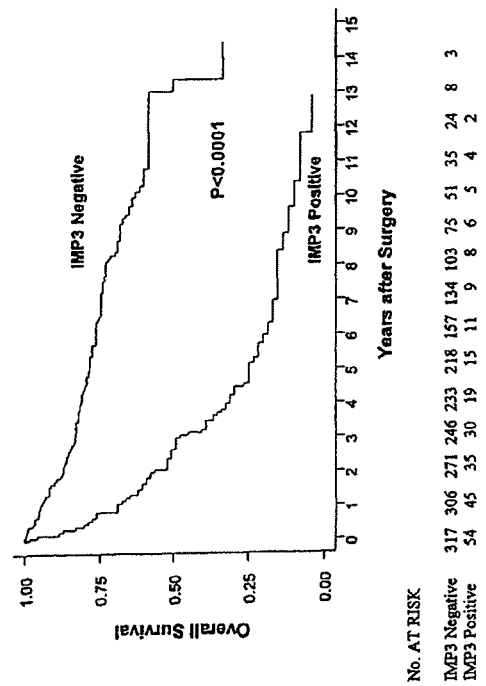
FIG. 4. Kaplan-Meier analysis of metastasis-free (A) and overall survivals (B) according to IMP3 status (positive verses negative) assessed by immunohistochemical analysis in total 371 patients with localized primary RCCs without metastasis during surgery. P values were calculated by using the log-rank test.
Figure 4:
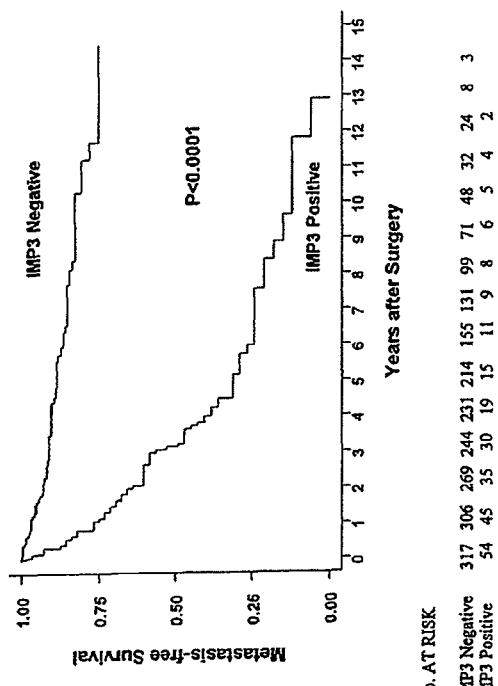

Kaplan-Meier plots and log-rank tests in all patients (n=371) with localized disease at the time of surgery and in these 371 patients separated into each stage (Stage I, n=216; Stage II, n=64; Stage III, n=91) showed that patients without IMP3 expression in their primary RCCs had significant longer metastasis-free survival and overall survival than patients with IMP3 expression. FIG. 4A showed that the 5-year metastasis-free survival rate was 89% in IMP3 negative patients versus 33% in IMP3 positive patients. The 5-year overall survival rate was 82% in patients without expression of IMP3 versus 27% in patients with IMP3 expression (FIG. 4B). In patients with stage I (FIGS. 5A and B), II (FIGS. 5C and D), and III (FIGS. 5E and F) renal cell cancers, the status of IMP3 expression was also significantly associated with increased risk of metastasis and was strongly linked to poor overall survival rate. Univariate analysis showed that hazard ratios (HR) of IMP3 expression were 9.22 (for metastasis-free survival; 95% confidence interval, 6.01-14.14; P<0.0001) and 5.66 (for overall survival; 95% confidence interval, 3.93-8.16; P<0.0001) respectively (Table 2). In patients whose localized RCCs were positive for IMP3 versus those with IMP3 negative RCCs, the 5-year metastasis-free survival were 44% vs. 98% [hazards ratio=17.18 (95% confidence interval: 7.82-37.78), stage I], 41% vs. 94% [10.14 (3.46-29.68), stage II] and 16% vs. 62% [4.04 (2.23-7.31), stage III], and the 5-year overall survival rates were 32% vs. 89% [6.44 (3.63-11.42), stage I], 41% vs. 88% [6.93 (2.63-18.27), stage II] and 14% vs. 58% [3.46 (1.98-6.05), stage III] respectively.

TABLE 2

Univariate Cox Proportional Hazard Regression Analysis for Metastasis-free and Overall Survival

| Variable | Metastasis-Free Survival | | Overall Survival | |
|---|---|---|---|---|
| | Hazard Ratio (95% CI) | P Value | Hazard Ratio (95% CI) | P Value |
| IMP3 Status (+ vs. −) | 9.22 (6.01-14.14) | <0.0001 | 5.66 (3.93-8.16) | <0.0001 |
| Age | 1.01 (1.00-1.03) | 0.167 | 1.03 (1.02-1.04) | <0.0001 |
| Sex (F vs. M) | 0.77 (0.48-1.21) | 0.250 | 0.94 (0.65-1.34) | 0.722 |
| Tumor Size | 1.16 (1.12-1.21) | <0.0001 | 1.10 (1.06-1.15) | <0.0001 |
| Tumor Stage | | | | |
| II vs. I | 1.85 (0.96-3.53) | 0.065 | 1.21 (0.72-2.02) | 0.470 |
| III vs. I | 6.05 (3.71-9.84) | <0.0001 | 3.39 (2.32-4.96) | <0.0001 |
| Tumor Grade | | | | |
| 2 vs. 1 | 4.40 (0.60-32.4) | 0.146 | 1.22 (0.52-2.87) | 0.646 |
| 3 vs. 1 | 11.37 (1.57-82.6) | 0.016 | 2.59 (1.12-6.01) | 0.027 |
| 4 vs. 1 | 18.44 (2.44-139.6) | 0.005 | 4.42 (1.78-10.96) | 0.001 |
| Histological type | | | | |
| Papillary vs. Clear | 0.48 (0.23-0.99) | 0.047 | 0.66 (0.39-1.12) | 0.121 |
| Chromophobe vs. Clear | 0.90 (0.39-2.08) | 0.808 | 0.75 (0.35-1.61) | 0.454 |

The IMP3 positive staining patterns (focal vs. diffuse) in the primary RCCs did not alter the patients' prognosis. There were no significant differences in metastasis-free survival (P=0.732) and overall survival (P=0.728) between patients with focal IMP3 staining and patients with diffuse IMP3 staining in their primary RCCs. No significant difference of overall survival is found between IMP3 positive and IMP3 negative patients with stage IV disease (P=0.14).

Multivariable Analysis

The results of the multivariable analysis, which was stratified by three different centers in this study, for metastasis-free survival and overall survival in the 371 patients with localized disease at the time of surgery are presented in Table 3. For these analyses, all factors shown in table 1 were initially included in the model as potential risk factors. Multivariable Cox proportional hazards regression analysis showed that the expression of IMP3 in primary RCCs was a strong independent predictor of the patients' clinical outcome. The hazard ratios were 5.84 (for metastasis-free survival; 95% confidence interval, 3.60 to 9.49; P<0.0001) and 4.01 (for overall survival; 95% confidence interval, 2.66 to 6.05; P<0.0001) respectively, which were much higher than the hazard ratios associated with all other independent risk factors (Table 3). In addition to IMP3 status, age and tumor stage III (compared to stage I) were also observed as significant risk factors for overall survival, and tumor size and tumor stage III (compared to stage I) were also observed as significant factors for metastasis-free survival (Table 3).

TABLE 3

Multivariable Cox Proportional Hazard Regression Analysis for Metastasis-free and Overall Survival

| Variable | Metastasis-Free Survival | | Overall Survival | |
|---|---|---|---|---|
| | Hazard Ratio (95% CI) | P Value | Hazard Ratio (95% CI) | P Value |
| IMP3 Status (+ vs. −) | 5.84 (3.60-9.49) | <0.0001 | 4.01 (2.66-6.05) | <0.0001 |
| Age | 1.00 (0.98-1.02) | 0.752 | 1.02 (1.01-1.04) | 0.006 |
| Sex | 1.08 (0.66-1.77) | 0.747 | 1.08 (0.73-1.59) | 0.694 |
| Tumor Size | 1.11 (1.04-1.18) | 0.001 | 1.05 (0.99-1.11) | 0.081 |
| Tumor Stage | | | | |
| II vs. I | 0.73 (0.30-1.77) | 0.484 | 0.87 (0.44-1.71) | 0.677 |
| III vs. I | 3.15 (1.72-5.77) | <0.0001 | 2.08 (1.30-3.33) | 0.002 |
| Tumor Grade | | | | |
| 2 vs. 1 | 2.02 (0.27-15.37) | 0.496 | 0.89 (0.37-2.16) | 0.797 |
| 3 vs. 1 | 4.43 (0.59-33.54) | 0.149 | 1.57 (0.64-3.84) | 0.319 |
| 4 vs. 1 | 3.22 (0.40-25.80) | 0.272 | 1.27 (0.47-3.44) | 0.634 |
| Histological type | | | | |
| Papillary vs. Clear | 0.50 (0.22-1.11) | 0.090 | 0.71 (0.41-1.25) | 0.236 |
| Chromophobe vs. Clear | 1.29 (0.54-3.08) | 0.564 | 0.95 (0.44-2.09) | 0.908 |

Discussion

Distant metastasis of renal cell carcinomas is the primary cause of death and therapeutic failure[1,2]. Although tumor stage, grade and subtype provide some prognostic information, the metastatic potential of localized RCC is often unpredictable. Since a well-characterized antibody to IMP3, but not IMP1 or IMP2, was available for immunohistochemical study, we investigated IMP3 expression in primary RCC and metastatic RCC as part of our program to develop biomarkers for clinical use. After we found that the expression of IMP3 was significantly increased in metastatic RCCs as compared to primary RCCs, we examined the relationship between IMP3 expression and progression in primary RCCs. Our findings demonstrate that the expression of IMP3 in primary renal cell carcinomas can predict tumor metastasis and provide important prognostic information in patients with localized disease who undergo nephrectomy.

IMP3 displays several features that make it an attractive prognostic marker for renal cell carcinoma. First, the expression of IMP3 is correlated with other known pathological indicators of aggressive RCCs. Our results showed that the expression of IMP3 was strongly related to higher tumor grade and stage, and larger tumor size.

Second, the expression of IMP3 in primary RCCs is independently linked to poor clinical outcome. Overall survival of patients with expression of IMP3 was extremely poor as compared to that of patients without IMP3 expression in primary localized RCCs and this was independent of tumor stage. Patients with IMP3 expression died at a rate 4 times greater than patients without IMP3 expression. Remarkably, the multivariate Cox analysis showed that the hazard ratios for death in patients with positive IMP3 in the primary tumor was much higher than the hazard ratios associated with any other clinical and pathological predictors including age, sex, and tumor stage, size, grade and subtype.

Third, the expression of IMP3 is an independent predictor of tumor metastasis. A decreased overall survival rate was strongly associated with a high metastatic rate in IMP3 positive patients. Out data showed that the expression of IMP3 was significantly increased not only in metastastic renal cell carcinomas but most importantly also in patients with primary renal cell cancers who developed metastatic disease as compared with renal cell cancers without metastasis. We found that 80% of patients with IMP3 positivity in their localized RCCs developed metastasis, whereas only 13% of patients without expression of IMP3 in their primary tumors developed metastases. In patients with stage III disease, almost all of IMP3 positive patients developed metastases after nephrectomy. In the multivariable Cox analysis, patients with IMP3 expression in their primary RCCs developed metastasis at a rate, which is 5.84 times greater than patients without expression of IMP3 adjusting for other well-known clinical variables.

Fourth, IMP3 immunohistochemical staining is a simple, inexpensive and reliable assay. As localized renal cell cancers are usually treated by partial or radical nephrectomy, tumor tissue is routinely available for immunohistochemical staining with the monoclonal L523S antibody. Our study showed that pathologists can readily analyze IMP3 immunohistochemisty without inter observer variation to determine positive and negative staining, which can be easily applied in routine clinical practice in all patients with nephrectomy. A computerized image analyzer for quantitative immunohistochemistry (ACIS), which has been clinically used for evaluation of Her2/neu gene expression, also confirmed the accuracy of the evaluation of the IMP3 immunostaining results by pathologists. In this study, we mainly focused on evaluation of IMP3 immunostaining by pathologists and used ACIS as a confirmatory test. A further study is necessary to determine how quantitative image analysis of immunostaining results correlates with patient outcome.

Fifth, as patients whose tumors express IMP3 have a high potential to develop metastasis, IMP3 provides a marker that not only can identify a subgroup of the patients who might benefit from a different follow-up approach after nephrectomy, but also can be used at initial diagnosis which would be the optimal time for considering early systemic therapy. Although the expression of IMP3 was found in multiple malignant tumors but not in adjacent benign tissues[11, 12, 15, 16], and a recent study demonstrated that IMP3 may have a critical role in the regulation of cell proliferation[17], little is known of the biological function of IMP3 in tumor pathogenesis. Our findings raise the possibility that IMP3, as an oncofetal protein, may play a direct role in the metastasis and/or more lethal behavior of renal cell carcinoma. Interestingly, Yaniv et al found that IMP3 in *Xenopus laevis*[13] is required for the migration of cells forming the roof plate of the neural tube and, subsequently, for neural crest migration[20]. The findings indicated that IMP3 plays an important role in promoting cell migration. Further study is required to investigate whether IMP3 plays a direct role in the biological behavior of metastatic RCC.

In summary, IMP3 serves as an excellent independent prognostic marker for renal cell carcinoma. IMP3 expression status in primary renal cell cancers may identify a subgroup of patients, particularly in patients with early-stage disease, who have a high potential to develop metastasis after surgery and die from the disease. The findings may have therapeutic implications in a group of patients who may benefit from early systematic therapy after nephrectomy.

REFERENCES

1. Motzer R J, Bander N H, Nanus D M. Renal-cell carcinoma.[see comment]. [Review] [150 refs]. *New England Journal of Medicine* 1996; 335(12):865-75.

2. Cohen H T, McGovern F J. Renal-cell carcinoma. [Review] [103 refs]. *New England Journal of Medicine* 2005; 353 (23):2477-90.
3. Chow W H, Devesa S S, Warren J L, Fraumeni J F, Jr. Rising incidence of renal cell cancer in the United States.[see comment]. *Jama* 1999; 281(17):1628-31.
4. Jemal A, Murray T, Ward E, et al. Cancer statistics, 2005. *Ca: a Cancer Journal for Clinicians* 2005; 55(1):10-30.
5. Tsui K H, Shvarts O, Smith R B, Figlin R A, deKernion J B, Belldegrun A. Prognostic indicators for renal cell carcinoma: a multivariate analysis of 643 patients using the revised 1997 TNM staging criteria. *Journal of Urology* 2000; 163(4):1090-5.
6. Sene A P, Hunt L, McMahon R F, Carroll R N. Renal carcinoma in patients undergoing nephrectomy: analysis of survival and prognostic factors. *British Journal of Urology* 1992; 70(2):125-34.
7. Couillard D R, deVere White R W. Surgery of renal cell carcinoma. [Review][83 refs]. *Urologic Clinics of North America* 1993; 20(2):263-75.
8. Thrasher J B, Paulson D F. Prognostic factors in renal cancer. [Review][66 refs]. *Urologic Clinics of North America* 1993; 20(2):247-62.
9. Rabinovitch R A, Zelefsky M J, Gaynor J J, Fuks Z. Patterns of failure following surgical resection of renal cell carcinoma: implications for adjuvant local and systemic therapy. *Journal of Clinical Oncology* 1994; 12(1):206-12.
10. Sandock D S, Seftel A D, Resnick M I. A new protocol for the followup of renal cell carcinoma based on pathological stage. *Journal of Urology* 1995; 154(1):28-31.
11. Lam J S, Shvarts O, Leppert J T, Figlin R A, Belldegrun A S. Renal cell carcinoma 2005: new frontiers in staging, prognostication and targeted molecular therapy. [Review] [75 refs]. *Journal of Urology* 2005; 173(6): 1853-62.
12. Zhao H, Ljungber B, Grankvist K, Rasmuson T, Tibshirani R, Brooks J D. Gene Expression Profiling Predicts Survival in Conventional Renal Cell Carcinoma. *PLoS Med* 2006; 3(1):e13.
13. Nielsen J, Christiansen J, Lykke-Andersen J, Johnsen A H, Wewer U M, Nielsen F C. A family of insulin-like growth factor II mRNA-binding proteins represses translation in late development. *Molecular & Cellular Biology* 1999; 19(2):1262-70.
14. Mueller-Pillasch F, Pohl B, Wilda M, et al. Expression of the highly conserved RNA binding protein KOC in embryogenesis. *Mechanisms of Development* 1999; 88(1): 95-9.
15. Monk D, Bentley L, Beechey C, et al. Characterisation of the growth regulating gene IMP3, a candidate for Silver-Russell syndrome. *Journal of Medical Genetics* 2002; 39(8):575-81.
16. Mueller-Pillasch F, Lacher U, Wallrapp C, et al. Cloning of a gene highly overexpressed in cancer coding for a novel KH-domain containing protein. *Oncogene* 1997; 14(22): 2729-33.
17. Wang T, Fan L, Watanabe Y, et al. L523S, an RNA-binding protein as a potential therapeutic target for lung cancer. *British Journal of Cancer* 2003; 88(6):887-94.
18. Yantiss R K, Woda B A, Fanger G R, et al. KOC (K homology domain containing protein overexpressed in cancer): a novel molecular marker that distinguishes between benign and malignant lesions of the pancreas. *American Journal of Surgical Pathology* 2005; 29(2):188-95.
19. Liao B, Hu Y, Herrick D J, Brewer G. The RNA-binding Protein IMP-3 Is a Translational Activator of Insulin-like Growth Factor II Leader-3 mRNA during Proliferation of Human K562 Leukemia Cells. *J. Biol. Chem.* 2005; 280 (18):18517-18524.
20. Yaniv K, Fainsod A, Kalcheim C, Yisraeli J K. The RNA-binding protein Vg1 RBP is required for cell migration during early neural development. *Development* 2003; 130 (23):5649-61.

Example 2

Association of IMP3 Tumor Expression with Clinicopathologic Features and Patient Outcome Among Patients with Papillary and Chromophobe Renal Cell Carcinoma Introduction IMP3 is a member of the insulin-like growth factor-II (IGF-II) mRNA binding protein family. Although IMP3 is expressed within developing epithelia, myocytes, and placenta during human and mouse embryogenesis, its expression is low or undetectable in post-natal tissues and virtually absent in adult tissues. IMP3 is thought to participate in the protection and intracellular distribution of IGF-II mRNA and, thus, has been implicated in regulating the production of IGF-II. Interestingly, some reports suggest that renal cell carcinoma (RCC) tumors, especially aggressive tumors exhibiting sarcomatoid differentiation, express increased IGF-II expression. Moreover, overexpression of IGF-IR, a cognate cell-surface receptor for IGF-I and II, has also been observed in RCC tumors and implicated as a feature of aggressive tumor behavior. Jiang et al.[1] systematically studied the expression of IMP3 in a cohort of 371 patients with localized tumors of the clear cell, papillary, or chromophobe RCC subtypes. In this study, Jiang et al.[1] reported that tumor cell IMP3 expression was significantly associated with progression to distant metastases and death, even after multivariate adjustment for patient age, sex, tumor size, stage, grade and histologic subtype. These findings were recently independently validated using a cohort of 629 consecutively-treated patients with localized clear cell RCC (Hoffmann et al, under review at Cancer Research). The various RCC subtypes including papillary RCC and chromophobe RCC have distinct genetic and morphologic characteristics.[2-5] Papillary and chromophobe RCCs accounts for approximately 25% of RCCs. Clear cell RCCs has worse cancer specific survival compared to papillary and chromophobe RCCs (ref 4). However, there is no large study for IMP3 expression in these various RCCs. The goal of the current study is to evaluate the association of IMP3 expression with clinicopathologic features and outcome using a multi-institutional cohort of patients with the papillary and chromophobe RCC subtypes.

Materials and Methods

Patient Selection

Using the combined resources of the Mayo Clinic, the University of Massachusetts Medical Center (UMMC), Massachusetts General Hospital (MGH), and City of Hope National Medical Center (CHNMC), we identified 334 patients treated with radical nephrectomy or nephron-sparing surgery for papillary or chromophobe RCC. The Mayo Clinic patients (N=246) were treated between 1990 and 1999, while the UMMC (N=39), MGH (N=38), and CHNMC (N=11) patients were treated between 1989 and 2003.[1] There were 254 (76.0%) patients with papillary RCC and 80 (24.0%) with chromophobe RCC.

Clinicopathologic Features

The clinicopathologic features studied included age, sex, histologic subtype classified according to the Union Internationale Contre le Cancer, American Joint Committee on Cancer, and Heidelberg guidelines[2,3], tumor size, primary tumor classification, regional lymph node involvement, distant metastases, the TNM stage groupings, and nuclear grade.

IMP3 Immunohistochemical Staining

Immunohistochemical studies were performed by the Department of Pathology at the UMMC on 5-um sections of formalin-fixed, paraffin-embedded tissue as previously described.[1] Antigen retrieval was carried out with 0.01 mol/L citrate buffer at pH 6.0, in an 800-W microwave oven for 15 minutes before immunostaining. The slides were stained on the DAKO Autostainer (DAKO Corporation, Carpinteria, Calif.) using the EnVision (Dako) staining reagents. The sections were first blocked for endogenous protein binding and peroxidase activity with an application of Dual Endogenous Block (Dako) for 10 minutes, followed by a buffer wash. The sections were then incubated with a mouse monoclonal antibody specific for IMP3 (L523S, Corixa, Seattle, Wash.) at a 2.0 μg/ml concentration for 30 minutes, followed again by a buffer wash. Sections were then incubated with the EnVision+ Dual Link reagent (a polymer conjugated with goat-anti-mouse-Ig, and horseradish peroxidase) for 30 minutes. The sections were then washed, and treated with diaminobenzidine (DAB) and hydrogen peroxide, which reacted to visualize the end product. A toning solution (DAB Enhancer, Dako) was used to enrich the final color. The sections were counterstained with hematoxylin, dehydrated, and cover-slipped with permanent media. Sections of urothelial carcinoma with known positivity of IMP3 were used as positive controls for the L523S mouse monoclonal antibody (MAb) specific for IMP3/KOC (Corixa Corporation, Seattle, Wash.) staining Negative control sections were stained by replacing the primary antibody with non-immune mouse IgG (Vector, Burlingame Calif.) at 2.0 ug/ml.

IMP3 Quantitation

IMP3 tumor expression was recorded as negative or positive after visual assessment by a genitourinary pathologist (ZJ) without knowledge of patient outcome.

Statistical Methods

Associations of IMP3 expression with clinicopathologic features were evaluated using Wilcoxon rank sum, chi-square, and Fisher's exact tests. Kaplan-Meier curves were used to visualize the associations of IMP3 expression with outcome. The magnitude of these associations were evaluated using Cox proportional hazards regression models and summarized with risk ratios and 95% confidence intervals (CI). Statistical analyses were performed using the SAS software package (SAS Institute; Cary, N.C.). All tests were two-sided and p-values <0.05 were considered statistically significant.

Results

There were 294 (88.0%) papillary or chromophobe RCC tumors with negative IMP3 expression and 40 (12.0%) with positive IMP3 expression. Comparisons of clinicopathologic features by IMP3 expression are summarized in Table 4. Positive IMP3 tumor expression was significantly associated with later tumor stage and higher tumor grade. For example, 70% of the IMP3-positive tumors were high grade (i.e., grade 3 or 4) compared with only 37% of the IMP3-negative tumors (p<0.001).

TABLE 4

Comparison of Clinicopathologic Features by IMP3 Tumor Expression for 334 Patients with Papillary and Chromophobe RCC

| | Tumor IMP3 Expression | | |
|---|---|---|---|
| Feature | Negative N = 294 | Positive N = 40 | P-value |
| | Median (Range) | | |
| Age at Surgery (Years) | 65 (21-89) | 63 (44-80) | 0.883 |
| Tumor Size (cm) | 4.1 (0.3-15.0) | 5.5 (0.7-25.0) | 0.090 |
| | N (%) | | |
| Sex | | | |
| Female | 68 (23.1) | 9 (22.5) | 0.929 |
| Male | 226 (76.9) | 31 (77.5) | |
| RCC Histologic Subtype | | | |
| Papillary | 228 (77.6) | 26 (65.0) | 0.081 |
| Chromophobe | 66 (22.5) | 14 (35.0) | |
| Primary Tumor Classification | | | |
| pT1 | 213 (72.5) | 21 (52.5) | 0.008 |
| pT2 | 49 (16.7) | 7 (17.5) | |
| pT3 | 31 (10.5) | 12 (30.0) | |
| pT4 | 1 (0.3) | 0 | |
| Regional Lymph Node Involvement | | | |
| pNX and pN0 | 289 (98.3) | 35 (87.5) | 0.003 |
| pN1 and pN2 | 5 (1.7) | 5 (12.5) | |
| Distant Metastases at Presentation | | | |
| pM0 | 289 (98.3) | 37 (92.5) | 0.058 |
| pM1 | 5 (1.7) | 3 (7.5) | |
| 2002 TNM Stage Groupings | | | |
| I | 211 (71.8) | 21 (52.5) | 0.002 |
| II | 48 (16.3) | 6 (15.0) | |
| III | 28 (9.5) | 7 (17.5) | |
| IV | 7 (2.4) | 6 (15.0) | |
| Nuclear Grade | | | |
| 1 | 9 (3.1) | 0 | <0.001 |
| 2 | 176 (59.9) | 12 (30.0) | |
| 3 | 103 (35.0) | 19 (47.5) | |
| 4 | 6 (2.0) | 9 (22.5) | |

There were 17 patients with papillary or chromophobe RCC who had extrarenal disease at nephrectomy, including 9 with regional lymph node involvement, 7 with distant metastases, and 1 with both. As such, associations of IMP3 expression with patient outcome were evaluated using the 317 patients with localized disease at nephrectomy (i.e., pNX/pN0; pM0; stage groups I, II, or III). In this subset, there were 284 (89.6%) papillary or chromophobe RCC tumors with negative IMP3 expression and 33 (10.4%) with positive IMP3 expression.

Twenty-eight of the 317 patients with localized disease progressed to distant metastases at a median of 3.1 years following nephrectomy (range 0-10).

Figure 6:
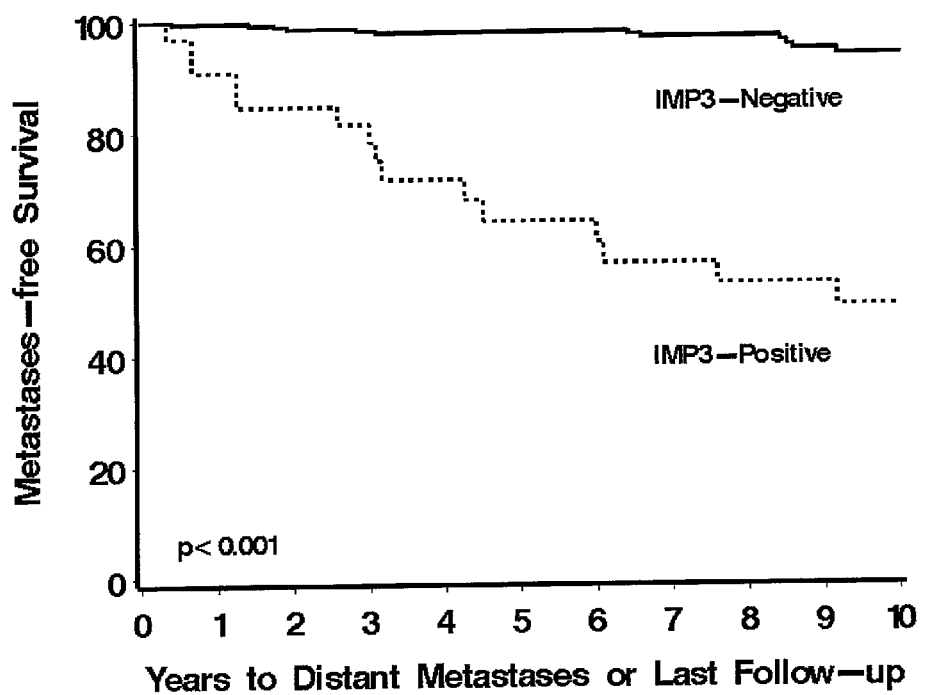
FIG. 6: Association of IMP3 tumor expression with progression to distant metastases for 317 patients with localized papillary and chromophobe RCC. Metastases-free survival rates (SE, number still at risk) at 5 and 10 years following nephrectomy were 63.9% (8.8%, 17) and 48.6% (9.5%, 12), respectively, for patients with IMP3-positive tumors compared with 97.7% (0.9%, 223) and 93.5% (1.9%, 86), respectively, for patients with IMP3-negative tumors.

Patients with localized IMP3-positive tumors were over 10 times more likely to progress to distant metastases compared with patients with localized IMP3-negative tumors (risk ratio 11.38; 95% CI 5.40-23.96; p<0.001; Table 5). In fact, 15 (45.5%) of the 33 patients with IMP3-positive tumors progressed compared with only 13 (4.6%) of the 284 patients with IMP3-negative tumors. Metastases-free survival rates (SE, number still at risk) at 5 and 10 years following nephrectomy were 63.9% (8.8%, 17) and 48.6% (9.5%, 12), respectively, for patients with IMP3-positive tumors compared with 97.7% (0.9%, 223) and 93.4% (1.9%, 86), respectively, for patients with IMP3-negative tumors (FIG. 6). In multivariate analysis adjusting for the TNM stage groupings and nuclear grade, patients with IMP3-positive tumors were still over 10 times more likely to progress compared with patients with IMP3-negative tumors (risk ratio 13.45; 95% CI 6.00-30.14; p<0.001; Table 5). IMP3 expression was univariately significantly associated with progression to distant metastases among patients with papillary RCC (risk ratio 9.14; 95% CI 3.39-24.64; p<0.001) as well as among patients with chromophobe RCC (risk ratio 11.91; 95% CI 3.58-39.61; p<0.001), although there were too few patients who progressed in these subsets to evaluate these associations in a multivariate setting.

TABLE 5

Associations of IMP3 Tumor Expression with Outcome for 317 Patients with Localized Papillary and Chromophobe RCC

| | Metastases-free Survival | | Overall Survival | |
|---|---|---|---|---|
| | Risk Ratio (95% CI) | P-value | Risk Ratio (95% CI) | P-value |
| Univariate IMP3 Expression | | | | |
| Negative | 1.0 (reference) | | 1.0 (reference) | |
| Positive | 11.38 (5.40-23.96) | <0.001 | 1.91 (1.13-3.22) | 0.016 |
| Multivariate TNM Stage Groupings | | | | |
| I | 1.0 (reference) | | 1.0 (reference) | |
| II | 4.38 (1.69-11.36) | 0.002 | 0.97 (0.55-1.68) | 0.900 |
| III | 10.94 (4.18-28.68) | <0.001 | 2.28 (1.29-4.04) | 0.005 |
| Nuclear Grade | | | | |
| 1 and 2 | 1.0 (reference) | | 1.0 (reference) | |
| 3 and 4 | 5.30 (1.94-14.49) | 0.001 | 1.38 (0.93-2.06) | 0.112 |
| IMP3 Expression | | | | |
| Negative | 1.0 (reference) | | 1.0 (reference) | |
| Positive | 13.45 (6.00-30.14) | <0.001 | 1.95 (1.15-3.31) | 0.013 |

At last follow-up 103 patients had died at a median of 4.5 years following nephrectomy (range 0-16). Among the 214 patients who were still alive at last follow-up, the median duration of follow-up was 8.8 years (range 0-16). Overall survival rates (SE, number still at risk) at 5 and 10 years following nephrectomy were 82.2% (2.2%, 240) and 65.4% (3.1%, 98), respectively. There was not a statistically significant difference in overall survival between patients with localized papillary and chromophobe RCC (p=0.997; log-rank test).

Figure 7:
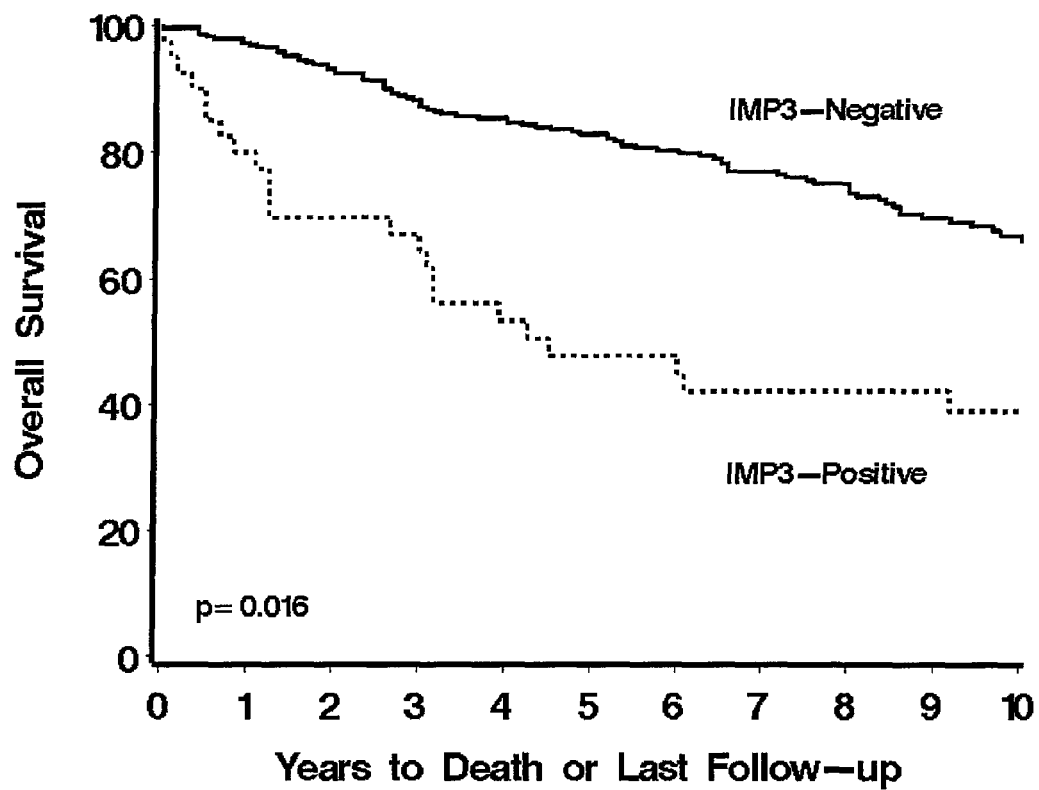
FIG. 7: Association of IMP3 tumor expression with death for 317 patients with localized papillary and chromophobe RCC. Overall survival rates (SE, number still at risk) at 5 and 10 years following nephrectomy were 57.9% (9.0%, 17) and 47.1% (9.2%, 12), respectively, for patients with IMP3-positive tumors compared with 85.0% (2.2%, 223) and 67.4% (3.3%, 86), respectively, for patients with IMP3-negative tumors.

Univariately, patients with localized IMP3-positive tumors were nearly twice as likely to die compared with patients with localized IMP3-negative tumors (risk ratio 1.91; 95% CI 1.13-3.22; p=0.016; Table 5). Seventeen (51.5%) of the 33 patients with IMP3-positive tumors died compared with 86 (30.3%) of the 284 patients with IMP3-negative tumors. Overall survival rates (SE, number still at risk) at 5 and 10 years following nephrectomy were 57.9% (9.0%, 17) and 47.1% (9.2%, 12), respectively, for patients with IMP3-positive tumors compared with 85.0% (2.2%, 223) and 67.4% (3.3%, 86), respectively, for patients with IMP3-negative tumors (FIG. 7). In multivariate analysis adjusting for the TNM stage groupings and nuclear grade, patients with IMP3-positive tumors were still nearly twice as likely to die compared with patients with IMP3-negative tumors (risk ratio 1.95; 95% CI 1.15-3.31; p=0.013; Table 5).

REFERENCES

1. Jiang Z, Chu P G, Woda B A, et al. Analysis of RNA-binding protein IMP3 to predict metastasis and prognosis or renal-cell carcinoma: a retrospective study. *Lancet Oncology* 2006; 7:556-564.
2. Storkel S, Eble J N, Adlakha K, et al. Classification of renal cell carcinoma: Workgroup No. 1. Union Internationale Contre le Cancer (UICC) and the American Joint Committee on Cancer (AJCC). *Cancer* 1997; 80:987-989.
3. Kovacs G, Akhtar M, Beckwith B J, et al. The Heidelberg classification of renal cell tumors. *Journal of Pathology* 1997; 183:131-133.
4. Cheville J C, Lohse C M, Zincke H, et al. Comparisons of outcome and prognostic features among histologic subtypes of renal cell carcinoma. *American Journal of Surgical Pathology* 2003; 27:612-624.
5. Lohse C M and Cheville J C. A review of prognostic pathologic features and algorithms for patients treated surgically for renal cell carcinoma. *Clinics in Laboratory Medicine* 2005; 25:433-464.

Example 3

Combination of Expression of IMP3 and Tumor Staging: A New System to Predict Metastasis for Patients with Localized Renal Cell Carcinomas Purpose:

We investigate whether the levels of expression of a new prognostic biomarker (IMP3) combined with tumor staging can serve as a new system to predict metastasis of localized renal cell carcinoma.

Design:

The 369 patients with localized RCCs from three institutions were investigated by use of survival analysis. The expression of IMP3 was evaluated by immunohistochemistry and a computerized image analyzer (Automated Cellular Imaging System). Combining quantitative IMP3 results with tumor staging (QITS system) generated four distinct groups of patients.

Result

Four groups of patients in QITS system showed significant differences for their metastasis-free (P<0.0001) and overall survivals (P<0.0001). Almost all patients of group IV with localized RCCs developed metastasis (sub clinical metastasis) and died after nephrectomy. The 5 and 10 year metastasis-free survival rates for the QITS groups were as follows for groups: I, 97% and 91%, II, 62% and 55%, III, 46% and 19%, and V, 17% and 4%, respectively. The 5 and 10 year overall survival rates for the QITS groups were as follows for groups: I, 89% and 72%, II, 58% and 41%, III, 38% and 17%, and V, 14% and 4%, respectively.

Conclusion:

Our findings suggest that combining quantitative IMP3 expression and tumor staging provide a unique, simple and accurate system to predict tumor metastasis. This system will provide important prognostic information for patients with localized RCCs and will help physicians to select high risk patients to start systematic therapy right after nephrectomy.

Introduction

Renal cell carcinoma accounts for about 85% of all malignant kidney tumors in the United States, making it the most common type of kidney cancer[1,2]. The incidence of this type of carcinoma has been rising steadily[3]. It was expected that about 38,890 new cases of kidney cancer would be diagnosed in the U.S. in 2006 with approximately 12,840 mortalities[4].

Currently surgical resection of tumor (nephrectomy) is the standard of care for almost all patients with renal cell carcinoma[1,2,5]. After nephrectomy, patients with metastatic disease typically receive systemic treatment (e.g. immunotherapy), which is associated with significant toxic side effects[1,2,5]. In order to avoid the multiple toxicities associated with treatment, watchful waiting is the standard of care following nephrectomy unless the patient presents with clearly metastatic disease[1,2,5]. Recently, two new drugs, Nexavar® (sorafenib) and Sutent® (sunitinib), the multi kinase receptor inhibitors, which can block the signal cascade of the vascular endothelial growth factor (VEGF) 2, 3 and R1, as well as platelet-derived growth factor (PDGF) that are critical to angiogenesis, have been used for treatment of patients with metastatic renal cell carcinoma[6-9]. However, these new drugs were only evaluated in patients with clinically metastatic RCC[6-9].

The metastatic potential of localized tumors is often unpredictable. Currently, evaluation of patients for post-nephrectomy adjuvant therapy relies almost entirely on clinical and pathological staging[10-13]. Renal cell cancers that are typically classified at the same stage exhibit markedly different biological behavior[10-13]. Consequently, 30% of patients with localized tumor during surgery will subsequently recur and metastasize and the survival rates of these are typically less than 10%[14,15]. Therefore, there is still a great need for biomarkers to predict patients' metastasis, particularly for early stages (stage I, II and III) of RCC. A reliable biomarker that can at the time of initial diagnosis of localized disease distinguish between tumors which will remain indolent following nephrectomy from those with early stage of tumor and a high probability for metastasis will allow clinicians to early target those individual patients who are most likely to benefit from adjuvant therapy, particularly from sorafenib and sunitinib therapy while sparing patients who are less likely to suffer metastasis from the side effects of systemic treatment.

IMP3 is a member of a family of conserved RNA-binding proteins that consists of IMP1, IMP2 and IMP3[16]. These IMP of proteins all contain two RNA recognition motifs and 4 K-homology domains that allow them to bind RNAs strongly and specifically, however only a few specific RNA targets, such as insulin-like growth factor II (IGF-II) have thus far been identified[17,18]. IMP3 has also been called KOC (K-homology domain protein over expressed in cancer) and L523S[17,19]. IMP3 is expressed in developing epithelium, muscle and placenta during early stages of human and mouse embryogenesis[16,18]. In contrast, it is expressed at low or undetectable levels in adult tissues. Certain cancers also express IMP3[17,19,20]. In fact, it was identified in screens for genes overexpressed in pancreatic and lung cancers[17,19,20]. It has been reported to be also expressed in carcinomas of the stomach and colon and soft tissue sarcomas[16]. Thus, IMP3 is an oncofetal antigen.

Recently, we have discovered that IMP3 is expressed in a subset of renal cell carcinomas and its expression predicts remarkably well the RCCs that progress to metastasis[21]. In previous study, we have demonstrated IMP3 status and tumor stage are the two most important risk factors for predicting metastasis of localized RCC. In this study, we used a computerized image analyzer [Automated Cellular Imaging System (ACIS)] to quantitative analysis of the immunohistochemistry IMP3 in localized RCCs and determined whether tumors with higher levels of IMP3 may progress more rapidly than those with lower levels of this molecule and whether combining the levels of IMP3 expression of IMP3 and tumor stage can serve as a new system to more accurately predict metastasis of localized renal cell carcinoma.

Materials and Methods

Patients and Tumor Specimens:

Formalin-fixed, paraffin-embedded samples from 369 patients with localized primary renal cell carcinomas, who underwent radical or partial nephrectomy, were obtained from the archival files at the University of Massachusetts Medical Center (UMMC, n=144), the Massachusetts General Hospital (MGH, n=147) and the City of Hope National Medical Center (CHNMC, n=78). The data from these sources represented all patients for whom archival tissues and adequate clinical follow-up information were readily available. All cases were collected between January of 1989 and December 2003 and the diagnoses were confirmed by at least two pathologists. Staging was based on pathological findings following the American Joint Committee on Cancer (AJCC) staging manual, sixth edition, 2002. Two hundred fifteen patients (pT1a or b) were stage I, 63 patients (pT2) were stage II, 91 patients (pT3a, N0, n=62; pT3b, N0, n=29) were stage III. Follow-up for this retrospective study was carried out by reviewing the patient clinical records. Overall survival was measured from the date of nephrectomy to the date of death or was censored as of the date of the last follow-up visit for survivors. Metastasis-free survival was measured from the date of surgery to the date of first clinical evidence of metastasis, and was censored at the date of death or the date of the last follow-up visit for survivors. The median follow-up was 63 months (range=1-174 months). The Institutional Review Board at each institution approved this study.

Immunohistochemical Analysis:

Immunohistochemical studies were performed on 5 μm sections of formalin-fixed, paraffin-embedded tissue from nephrectomy specimens by using an avidin-biotinylated peroxidase complex system as a previously published protocol[20] on the DAKO Autostainer (DAKO Corporation, Carpinteria, Calif.). Sections of pancreatic carcinoma with known positivity of IMP3 were used as positive controls for the L523S mouse monoclonal antibody (MAb) specific for IMP3/KOC (Corixa Corporation, Seattle, Wash.) staining Negative controls were performed by replacing the primary antibody with nonimmune IgG.

Quantitative Analysis of Immunostaining:

A total of 1,845 tumor areas (5 different areas/case) from all RCC tissues were quantitatively analyzed by a computerized image analyzer (Automated Cellular Imaging System, ACIS, ChromaVision Medical System Inc., San Juan Capistrano, Calif.) to evaluate the IHC results. With ACIS, positive staining is calculated by applying two thresholds with one recognizing blue background (hematoxylin stained) cells and another recognizing brown positive cells. The integrated optical density (IOD) is that the sum of brown pixels times brown intensity of those pixels. The ACIS values were calculated as IOD was divided by the sum of the blue area and the brown area. IMP3 expression in RCCs was considered to be negative (average ACIS value/case: <1) and positive (average ACIS value/case: ≥1; low levels of expression: ACIS values=1 to 10, and high levels of expression: ACIS values >10).

Statistical Analysis:

Age, sex, size of the tumor, tumor stage and grade, and IMP3 status were collected as baseline variables. The distribution of each baseline variable was compared for IMP3-positive and IMP3-negative subgroups with the Wilcoxon rank sum test for continuous variables and the Fisher's exact test for categorical variables. Overall survival and metastasis-free survival of 369 patients were estimated by the Kaplan-Meier method and evaluated with the use of log-rank test for univariate analysis. The Cox proportional-hazard model was used to assess the simultaneous contribution of the following baseline covariates of age, sex, size of the tumor, tumor stage and grade, and IMP3 status. A two-sided P-value of less than 0.05 was considered to indicate the statistical significance. Based on a Cox proportional-hazard model, IMP3 status and tumor stage were the two most important independent risk factors for predicting metastasis of localized RCC, the levels (low versus high) of IMP3 expression from ACIS analysis and tumor stage were divided into five subgroups each of which had a significantly increasing risk of metastasis and death over the previous one.

Results

Figure 8:
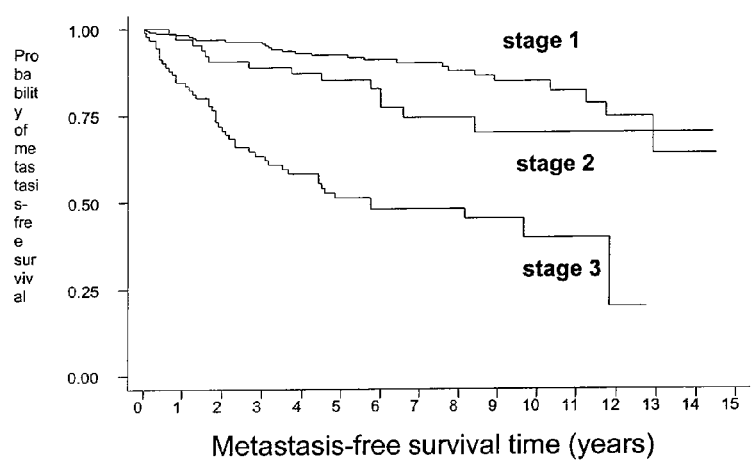
FIG. 8 shows the probability of metastasis free survival as a function of metastasis-free survival time (years) for stage 1, 2 and 3 RCCs.
Figure 9:
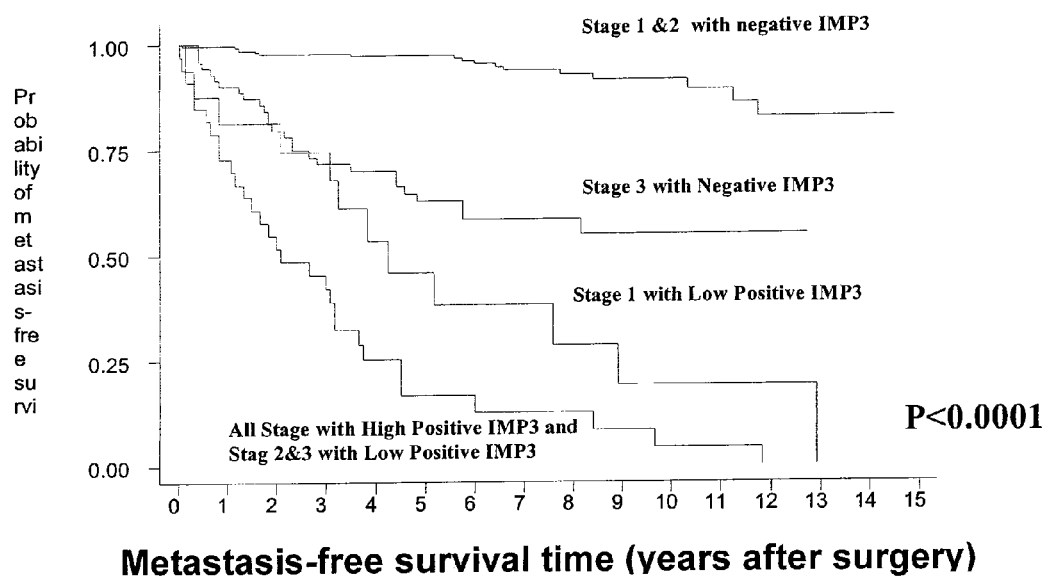
FIG. 9 shows the shows the probability of metastasis free survival as a function of metastasis-free survival time (years after surgery) for stages 1, 2 and 3 RCCs and negative, low positive or high positive IMP3 expression.
Figure 10:
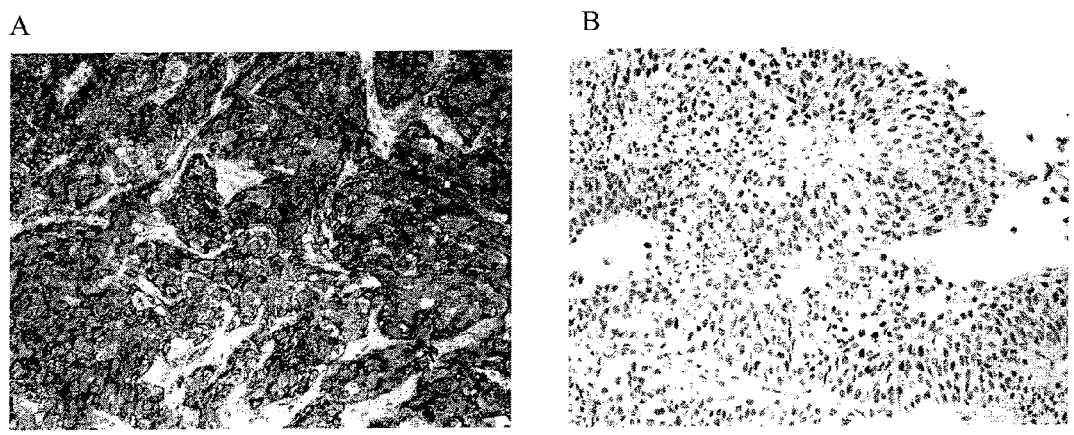
FIG. 10. Immunohistochemical stains for IMP3 showing that high grade UC (A) was positive for IMP3 while low grade UC (B) was negative for IMP3.
Figure 11:
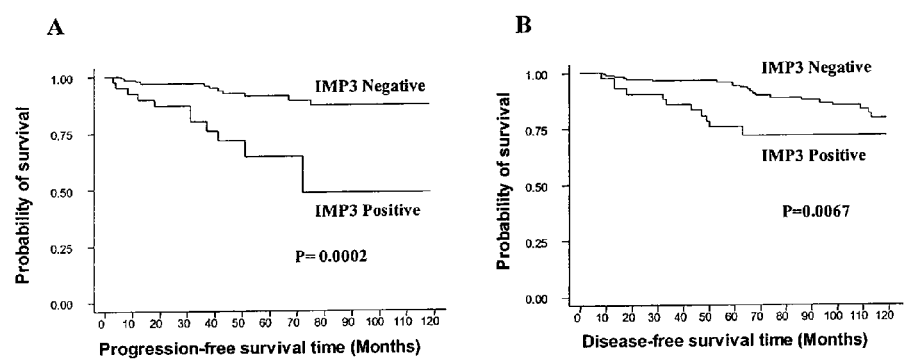
FIG. 11. Kaplan-Meier analysis of progression-free (A) and disease-free survival (B) in patients with superficial urothelial carcinomas (Ta, T1 and Tis). P values were calculated by using the log-rank test.
Figure 12:
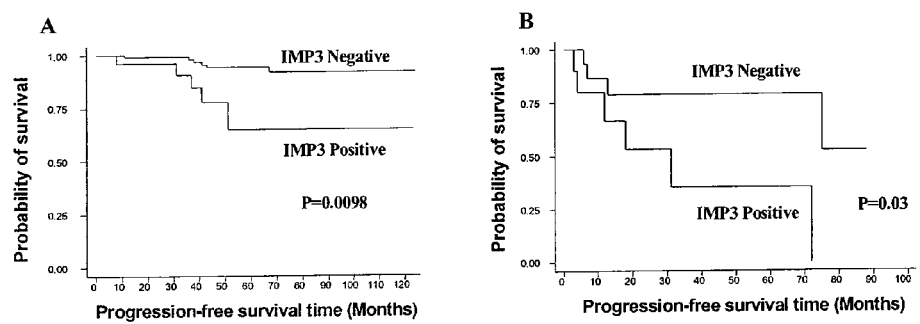
FIG. 12. Kaplan-Meier analysis of progression-free survivals in patients with Ta superficial urothelial carcinomas (A) and T1 superficial urothelial carcinomas (B). P values were calculated by using the log-rank test.
Figure 13:
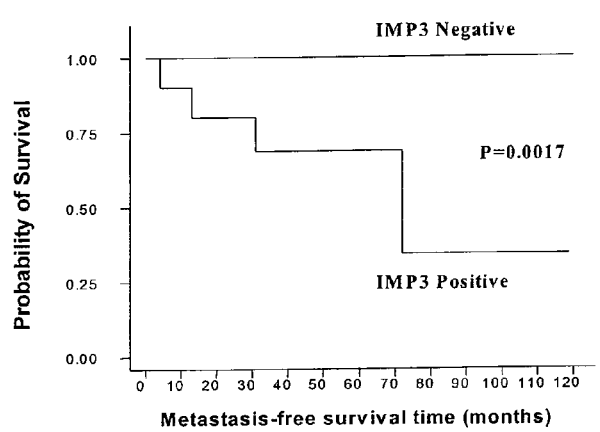
FIG. 13. Kaplan-Meier analysis of metastasis-free survivals in patients with T1 superficial urothelial carcinomas. P values were calculated by using the log-rank test.

Patients based on IMP3 status of their RCCs including negative, low and high expression, and tumor stage were classified into four groups (Tables 6 and 7). This QITS system showed significant differences for their metastasis-free (P<0.0001) and overall survivals (P<0.0001). FIG. 9 showed significant stratification of high risk patients compared to TNM staging alone (FIG. 8). Almost all patients of group IV with localized RCCs developed metastasis (sub clinical metastasis) and died after nephrectomy (FIG. 9). The 5 and 10 year metastasis-free survival rates for the QITS groups were as follows for groups: I, 97% and 91%, II, 62% and 55%, III, 46% and 19%, and V, 17% and 4%, respectively (Table 7). The 5 and 10 year overall survival rates for the QITS groups were as follows for groups: I, 89% and 72%, II, 58% and 41%, III, 38% and 17%, and V, 14% and 4%, respectively (Table 8).

TABLE 6

Quantitative IMP3 Status of RCC Combined with Tumor Stage (QITS) System

| QITS Groups | IMP3 Status | Tumor Stage |
| --- | --- | --- |
| I | Negative | Stage 1 and 2 |
| II | Negative | Stage 3 |
| III | Low Expression | Stage 1 |
| IV | Low Expression | Stage 2 and 3 |
|  | High Expression | Stage 1, 2 and 3 |

TABLE 7

QITS and TNM Systems with 5- and 10 Year Metastasis-free Survivals

| | QITS Groups | | | |
| --- | --- | --- | --- | --- |
| | I | II | III | VI |
| 5-Year Metastasis free Survival | 97% | 63% | 46% | 17% |
| 10-Year Metastasis free Survival | 91% | 55% | 19% | 4% |

| | TNM Stage | | |
| --- | --- | --- | --- |
| | I | II | III |
| 5-Year Metastasis free Survival | 92% | 85% | 51% |
| 10-Year Metastasis free Survival | 84% | 69% | 40% |

TABLE 8

QITS and TNM Systems with 5- and 10 Year Overall Survivals

| | QITS Groups | | | |
| --- | --- | --- | --- | --- |
| | I | II | III | VI |
| 5-Year Metastasis free Survival | 89% | 58% | 38% | 14% |
| 10-Year Metastasis free Survival | 72% | 41% | 17% | 4% |

| | TNM Stage | | |
| --- | --- | --- | --- |
| | I | II | III |
| 5-Year Metastasis free Survival | 83% | 80% | 47% |
| 10-Year Metastasis free Survival | 67% | 58% | 30% |

Example 4

IMP3, an Oncofetal Protein, Promotes Tumor Invasion and Predicts Progression of Cervical Intraepithelial Neoplasia into Invasive Cancer Introduction Despite decades of effort, cervical cancer remains the second leading cause of cancer related death in women at 288,000 per year worldwide[1]. Cervical squamous intraepithelial lesion (SIL)[2] or cervical intraepithelial neoplasia (CIN)[3] is a precancerous condition, and its treatment can prevent the development of invasive cervical carcinomas[2]. It is evident that morphologically defined squamous intraepithelial lesions represent a heterogeneous group and that progression of high grade squamous intraepithelial lesions (HGSIL) into invasive squamous cell carcinoma is unpredictable. Currently, it is estimated that about 10-30% of HGSIL will develop into invasive carcinomas if left untreated[4, 5, 6]. Standard treatments for all patients with HGSIL are local excisional surgical procedures, such as the loop electrical excision procedure (LEEP) or cold knife cone excision[7]. These procedures can damage the cervical stroma in ways that lead to cervical stenosis or incompetence[8, 9, 10]. This can cause significant morbidity for women of child-bearing age, increasing the risk of preterm delivery, low birth-weight infants and premature rupture of membranes[8, 9, 10]. Currently, approximately 750,000 women are diagnosed with squamous intraepithelial lesions each year in the United States, and the majority of these patients undergo surgical treatment[11,12]. If the majority (approximately 70-80%) of high grade squamous intraepithelial lesions that will not develop into invasive cancer could be identified, then these patients could be spared the current surgical procedure. This would benefit the outcome of any future pregnancies in this group of women[8, 9, 10] and also reduce health care costs. Therefore, it is very important to establish methods to identify squamous intraepithelial lesions that have the potential to progress to invasive cancer. Although many efforts have been made, especially in developing biomarkers, to selectively identify high risk patients[13, 14] there has been limited success[15, 16].

Methods

Patients and Tumor Samples

We obtained formalin-fixed, paraffin-embedded tissue samples from 1249 patients with cervical biopsies (n=947), and LEEP/hysterectomy (n=302), from the archives at the University of Massachusetts Medical Center, Worcester, Mass., USA. Among 1249 patients, 79 patients were diagnosed invasive squamous cell carcinoma, 895 patients were HGSIL, 108 patients were low grade SIL (LGSIL), and 167 patients were negative for dysplasia (Table 1). To study the expression of IMP3 in all cervical lesions, we first obtained 586 cases of cervical lesions (no dysplasia, N=167; LGSIL, N=108; HGSIL, N=223 and invasive squamous cell carcinoma, N=79) between January 1997, and July 2007. To study IMP3 positivity in squamous intraepithelial lesions for the detection of a high risk group of patients with HGSILs who will develop invasive carcinomas, we studied all patients with cervical biopsies diagnosed as HGSIL and with subsequent LEEP or hysterectomy (N=710) between January 1997 and December 2006 for our clinical follow-up study.

Immunohistochemical Analysis

Immunohistochemical studies were performed on 51 μm sections of formalin-fixed, paraffin-embedded tissue from cervical biopsy, excisional biopsy and hysterectomy specimens. Antigen retrieval was carried out with 0.01 mol/L citrate buffer at pH 6.0, in an 800-W microwave oven for 15 minutes before immunostaining. The slides were stained on the DAKO Autostainer (DAKO Corporation, Carpinteria, Calif.) using the EnVision (DAKO) staining reagents. The sections were first blocked for endogenous protein binding and peroxidase activity with an application of Dual Endogenous Block (DAKO) for 10 minutes, followed by a buffer wash. The sections were then incubated with a mouse monoclonal antibody specific for IMP3 (L523S, DAKO) at a 2.0 μg/ml concentration for 30 minutes. Sections were then incubated with the EnVision+Dual Link reagent (a polymer conjugated with goat-anti-mouse-Ig, and horseradish peroxidase) for 30 minutes, and treated with diaminobenzidine (DAB) and hydrogen peroxide, to produce the visible brown pigment. The sections were counterstained with hematoxylin, dehydrated, and coverslipped with permanent media. Sections of urothelial carcinoma with known positivity of IMP3 were used as positive controls for IMP3 staining. Negative controls were performed by replacing the primary antibody with nonimmune IgG.

Morphological Evaluation

The diagnosis of low and high grade CIN, and SCC was established by examination of hematoxylin and eosin stained sections by two pathologists (DL and ZJ). Positive staining of IMP3 was defined as a dark brown cytoplasmic staining pattern in the tumor epithelial cells, which was easily observed at low power magnification (<40×). Scant fine granular background staining of epithelial cells, which cannot be seen at low power magnification (≤40×), or no staining at all was considered negative.

Cell Culture and Small Interference RNA (siRNA) Transfection

The cervical cancer cell line (HeLa cell) was maintained in DMEM with high glucose (GIBCO, Carlsbad, Calif.), containing 10% FBS and antibiotics at 37° C. incubator with 5% $CO_2$. For siRNA transfection, $2 \times 10^5$ cells were passed into antibiotic-free DMEM media in a E-well plate. On the next day, 20 or 40 nM of non-target siRNA or SMARTpool siRNA of human IMP3 (Dharmacon, Lafayette, Colo.) were transfected into HeLa cells with Lipofectamine 2000 (Invitrogen, Carlsbad, Calif.), according to the manufactor protocol. All transfected cells were grown in a 37° C. incubator with 5% $CO_2$ for up to 72 hours for future experiments. To assess transfection efficiency, Block-It™ Fluorescent oligo (Invitrogen) was transfected under the same condition for control or IMP3 siRNA. Transfected cells were photographed under phase-contrast microscope.

RT-PCR

To assess IMP3 knockdown efficiency by RT-PCR, siRNA transfected HeLa cells were trypsinized and collected for total RNA extraction using RNeasy Mini kit (QIAGEN, Valencia, Calif.). Two micrograms of total RNA was used for reverse transcription using SuperScript III (Invitrogen). For RT-PCR, 2 μl of reverse-transcribed first-strand cDNA were used in each PCR reaction with HotStar Taq Plus Master Mix (QIAGEN). RT-PCR primers for IMP3 were: forward 5'-AGTGGGAGGTGCTGGATAGTT (SEQ ID No. 9) and reverse 5'-CTGGGTCTGTTTGGTGATGTT (SEQ ID No. 10). PCR program was as follows: 95° C. for 5 minutes, followed by 95° C. for 30 seconds, 58° C. for 30 seconds, 72° C. for 30 seconds with a total of 26 cycles. PCR products were resolved into 1.2% agarose gel and photographed under UV illumination. GAPDH served as the loading control.

Western Blot Analysis

To assess the level of IMP3 protein expression after knockdown, Western blotting was performed according to our previous method[26]. Briefly, an aliquot of HeLa cells transfected with control siRNA or siIMP3 for 72 hours was re-suspended into RIPA butter (Boston BioProduct, Boston, Mass.) with complete protease inhibitors (Roche Diagnostics, Mannheim, Germany) for whole cell extract. A total of 30 μg of proteins was resolved into 10% SDS-PAGE gel for IMP3 Western blotting, using a mouse monoclonal primary antibody against human IMP3 (DAKO) and anti-Actin (Santa Cruz Biotechnology, Santa Cruz, Calif.) served as the loading control.

Cell Proliferation Assay

To examine cell proliferation after IMP3 knockdown, cell proliferation reagent WST-1 (Roche Diagnostics) was used according to the manufactor's instructions. Briefly, $5 \times 10^3$ HeLa cells were seeded into each well of a 96-well plate in a final volume of 100 μl/well, and cells were cultured in a 37° C. incubator with 5% $CO_2$. On the next day, cells were transfected with Control or siIMP3 using Lipofectamine 2000. At 24, 48, and 72 hours of siRNA transfection, 10 μl of WST-1 were added directly into each well and cells were incubated in a 37° C. incubator with 5% $CO_2$ for 1 hour. The absorbance of each well was measured with a Beckman Coulter DTX 880 Multimode Detector (Beckman, Miami, Fla.) at a wavelength of 450 nm and reference wavelength of 620 nm. An average absorbance (0D450-0D620) was calculated based on ten independent samples.

Cell Migration Assay

HeLa cell migratory ability was assessed by the Transwell assay as described previously with minor modification[33]. Briefly, Transwell (Corning Incorporated, Corning, N.Y.) was coated with 15 μg/ml Laminin (BD Biosciences, San Jose, Calif.) at 4° C. overnight and then blocked by plain DMEM media for 1 hour at 37° C. incubator. HeLa cells transfected with either Control or siIMP3 for 72 hours were trypsinized and re-suspended into DMEM with 2.5% filtered BSA to a concentration of $4 \times 10^5$ cells/ml. One hundred microliter of the cells were seeded into each Transwell that was incubated in a 24-well plate containing 600 μl/well of NIH3T3 conditioned media. Cells were cultured in a 37° C. incubator with 5% $CO_2$ for 4 hours. Cells inside the Transwell were swabbed by a Q-tip followed by fixation in methanol for 10 minutes at room temperature. Each Transwell was rinsed 5 times in distilled water and the inside was swabbed again by a Q-tip. After air-drying, each Transwell was put onto 20 μl of mounting medium containing DAPI (Vector Laboratories, Burlingame, Calif.) on a cover slip. Migratory cells outside the bottom of the Transwell were visualized under a fluorescent microscope at 20× magnification. For quantification, five representative fields were photographed and total number of cells was counted. Results were reported as an average of six independent samples.

Statistical Analysis

Invasive cancer-free survival rates by IMP3 status of all patients (N=710) with HGSIL in their cervical biopsies undergoing LEEP or hysterectomy were estimated by the Kaplan-Meier method and evaluated using log-rank test for univariate analysis. Invasive cancer-free survival was measured from the date of cervical biopsy to the date of diagnosis of invasive carcinoma by LEEP or hysterectomy. As the standard treatment in the United States for all patients with HGSIL is local excisional surgical procedures (e.g. LEEP) or hysterectomy after a diagnosis of HGSIL[(4)]. Most of our patients with HGSILs were treated by a resection procedure soon after their diagnoses. The median follow-up time was 44 days (range=2 to 880 days). The median follow-up time for the IMP3 negative group (N=551) was 46 days (range=2 to 880 days) and for the IMP3 positive group (N=159) was 41 days (range=4 to 810 days). The distribution of every baseline variable was compared between IMP3 positive and IMP3 negative subgroups using a Student's t-test for continuous variables and Fisher's exact test for categorical variables. A two-sided P-value of less than 0.05 was considered to indicate the statistical significance.

Results

IMP3 Expression is Significantly Elevated in Invasive Cancer and a Small Group of HGSILs.

TABLE 9

Clinicopathological Characteristics of Cervical Squamous Intraepithelial Lesion (SIL) and Invasive Cancer Patients (N = 1249)

| Characteristic | IMP3+ (n = 216) | IMP3− (n = 1033) | p-value |
| --- | --- | --- | --- |
| Age (years) | 34.93 ± 11.86 | 34.85 ± 11.61 | 0.928* |
| Diagnosis | | | <0.0001** |
| No Dysplasia | 0 (0%) | 167 (100%) | |
| Low Grade SIL | 0 (0%) | 108 (100%) | |
| High Grade SIL | 140 (16%) | 755 (84%) | |
| Invasive Cancer | 76 (96%) | 3 (4%) | |

*Student's t-test;
**Fisher's exact test.

Table 9 provides the relevant clinical characteristics of 1249 patients with cervical lesions. Age was not associated with IMP3 status (P=0.928). IMP3 expression was strongly associated with HGSIL and invasive squamous carcinoma. The expression of IMP3 was found in the cytoplasm of HGSIL cells and invasive tumor cells. IMP3 expression was not identified in patients with LGSIL (N=108) or negative for dysplasia (N=167, Table 9). In contrast, 76 (96%) of 79 invasive cancers showed IMP3 expression (Table 9). 140 of the 895 (16%) patients with HGSIL were positive for IMP3 (Table 9).

Prognostic Value of IMP3 in HGSIL for Invasive Cancer 710 patients who had HGSIL without invasive cancer in their cervical biopsies and had follow-up LEEP or hysterectomy were included in our follow-up study. A small portion [38 of 710 (5%)] of patients were found to have invasive cancer in their follow-up LEEP or hysterectomy. IMP3 expression was found in 159 of 710 (22%) HGSILs and 551 of 710 HGSILs (78%) were negative for IMP3. Kaplan-Meier invasive cancer-free survival curves showed that no patients (N=551) with IMP3-negative HGSILs had invasive cancer whereas 38 of 159 (24%) patients with IMP3-positive HGSILs in their cervical biopsies were shown to have invasive cancer in their follow-up LEEP or hysterectomy (P<0.0001).

IMP3 Promotes the Migration of Cervical Cancer Cells

We next analyzed the potential role of IMP3 in promoting the migration of cervical cancer cells in vitro. To test the hypothesis that IMP3 may play a role in cancer cell migration, we used the human cervical cancer (HeLa) cell line as a model. These cells, which express IMP3, were transfected with either 20 or 40 nM of SMARTpool small interfering RNA for IMP3 (siIMP3) or a non-targeting pool of siRNA (Control) for 72 hours. The siRNA transfection efficiency was confirmed by transfection of Block-It™ FITC labeled siRNA, in which approximately 90% of cells gained green fluorescence (data not shown). We observed that IMP3 mRNA and protein expression was reduced significantly by siIMP3 in comparison to the control siRNA. To determine whether IMP3 silencing affected the migration of HeLa cells, a Transwell migration assay was performed 72 hours after transfection of siIMP3 or control siRNA. Transfection of siIMP3 caused a marked reduction in HeLa cell migration in comparison to control siRNA (FIG. 3C). A two-tail Student T-test showed that this difference is significant ($p=2.5 \times 10^{-8}$). However, the reduction of IMP3 did not alter the growth rate of HeLa cells as indicated by WST-1 cell proliferation assay.

Discussion

In this study, we demonstrate that the expression of IMP3 in cervical cancer cells is highly associated with invasive capability and IMP3 expression in the high-grade intraepithelial lesions is predictive of tumor invasion. Therefore, IMP3 is able to serve as a biomarker which will provide important prognostic information for patients with pre-invasive cervical lesions.

There are several attractive features for the use of IMP3 expression as a biomarker in cervical lesions. First, the expression of IMP3 was significantly increased not only in invasive squamous cell carcinoma but most importantly also in a subgroup of patients with high grade dysplasia who have invasive cancer in their follow-up excisional biopsies. We found that 24% of patients with IMP3 positivity in their HGSILs have invasive cancer in their follow-up tissue resections. Therefore, the expression of IMP3 in cervical biopsies can identify a subgroup of patients who are at risk of progressing into invasive carcinomas.

Second, we have demonstrated that the sub group of IMP3-negative HGSILs is not associated with invasive carcinoma. All 551 patients with IMP3-negative HGSILs were invasive cancer free in their follow-up tissue resections. Therefore, IMP3-negative HGSIL has a 100% negative predictive value for invasive cancer. As far as we know, there have not been any other biomarkers reported for cervical lesions that have such a powerful negative predictive value. If these findings are validated in additional clinical trials then it might be possible to change the follow-up procedures from LEEP to follow-up biopsy and observation for those patients with IMP3-negative HGSILs in their biopsies. The obvious importance of identifying patients at low risk of cancer progression is that it would both spare them the morbidity of the surgical procedures, and also save the health care system money.

Third, IMP3 immunohistochemical staining is a simple, inexpensive and reliable test. As most patients with high-grade dysplasias undergo biopsy, cervical biopsy tissue is routinely available for immunohistochemical staining so that this assay could be easily applied in routine clinical practice for all patients with cervical biopsies. Fourth, our in vitro assays strongly support our clinical data that IMP3 may play an important role in cancer cell invasion. A previous study showed that IMP family members can control cancer cell invasion in vitro[32]. We confirm and extend this analysis to show that reduction of IMP3 expression alone in cervical cancer cells is able to significantly decrease cancer cell migration. Our findings should enhance the understanding on cervical cancer oncogenesis as well. The established three pathogenetic steps in cervical carcinogenesis include infection of high-risk type HPV, initiation of clonal expansion of neoplastic cells with deregulated expression of viral oncogenes, and finally progression into tumor invasion[4, 6]. Molecular markers associated with step 1 and 2 may have been identified[13, 14, 15, 16]. IMP3 could be a crucial factor that is involved in the migration event from the intraepithelial neoplastic cells into the invasive cancer. Exactly how IMP3 might regulate these processes is not defined by our studies but it has been suggested that IMP proteins regulate the expression of molecules involved in adhesion and invasion, presumably through RNA binding[32]. There is currently no evidence of association between HPV infection and IMP3 expression.

In summary, our study suggests that IMP3 is the first specific molecular marker that identifies the invasive potential of cervical squamous intraepithelial lesions. This finding is significant as it may impact current clinical practice. It provides a real possibility of an entirely new molecular approach in examining cervical cancer precursors rather than our current morphological classification. Such a new approach could improve cervical cancer prevention by reducing the prevalence of non-necessary surgeries and provide a simple, cost-efficient molecular and biological testing method, which may reduce cervical cancer related healthcare costs that are currently at estimated at 6 billion dollars each year in the United States alone and more than the combined costs of all other female related cancers (34)

REFERENCES

1. Cervical cancer facts and figures—2006, vol. 2006: American Cancer Society, 2006.
2. The 1988 Bethesda System for reporting cervical/vaginal cytological diagnoses. National Cancer Institute Workshop. JAMA 1989; 262:931-4.
3. Richart R M. Cervcal intraepithelial neoplasia: a review. In: Sumners S C (ed) Pathology annual. Appleton-Century-Crofts, East Norwalk; 1973. p 301-328.
4. Holowaty P, Miller A B, Rohan T, To T. Natural history of dysplasia of uterine cervix. Natl Cancer Inst 1999; 91:252-258.
5. Gad C. The management and natural history of severe dysplasia and carcinoma in-situ of the uterine cervix. Br. J. Obstet Gynecol 1976; 83:554-559.
6. McCredie M R, Sharples K J, Paul C, Baranyai J, Medley G, Jones R W, et al. Natural history of cervical neoplasia and risk of invasive cancer in women with cervical intraepithelial neoplasia 3: a retrospective cohort study. Lancet Oncol 2008; 9(5):425-34.
7. Wright T C Jr, Massad L S, Dunton C J, Spitzer M, Wilkinson E J, Solomon D. 2006 American Society for Colposcopy and Cervical Pathology-sponsored Consensus Conference: 2006 consensus guidelines for the management of women with cervical intraepithelial neoplasia or adenocarcinoma in situ. Am J Obstet Gynecol 2007; 197(4):340-5.
8. Kyrgiou M, Tsoumpou I, Vrekoussis T, Martin-Hirsch P, Arbyn M, Prendiville W, et al. The up-to-date evidence on colposcopy practice and treatment of cervical intraepithelial neoplasia: the Cochrane colposcopy & cervical cytopathology collaborative group (C5 group) approach. Cancer Treat Rev 2006; 32(7):516-23.
9. Kyrgiou M, Koliopoulos G, Martin-Hirsch P, Arbyn M, Prendiville W, Paraskevaidis E. Obstetric outcomes after conservative treatment for intraepithelial or early invasive cervical lesions: systematic review and meta-analysis. Lancet 2006; 367(9509):489-98.
10. Sadler L, Saftlas A, Wang W, Exeter M, Whittaker J, McCowan L. Treatment for cervical intraepithelial neoplasia and risk of preterm delivery. JAMA 2004; 291(17): 2100-6.
11. Sjoborg K D, Vistad I, Myhr S S, Svenningsen R, Herzog C, Kloster-Jensen A, et al. Pregnancy outcome after cervical cone excision: a case-control study. Acta Obstet Gynecol Scand 2007; 86(4):423-8.
12. Davey D D, Neal M H, Wilbur D C, Colgan T J, Styer P E, Mody D R. Bethesda 2001 implementation and reporting rates: 2003 practices of participants in the College of American Pathologists Interlaboratory Comparison Program in Cervicovaginal Cytology. Arch Pathol Lab Med 2004; 128(11):1224-9.
13. von Knebel-Doeberitz M. New markers for cervical dysplasia to visualize the genomic chaos created by aberrant oncogenic papillomavirus infections. Eur J Cancer 2002; 2229-42.
14. Wentzensen N, von Knebel-Doeberitz M. Biomarkers in cervical cancer screening. Dis Markers 2007; 23(4):315-30.
15. Wang S S, Trunk M, Schiffman M, Herrero R, Sherman M E, Burk R D, et al. Validation of p16INK4a as a marker of oncogenic human papillomavirus infection in cervical biopsies from a population-based cohort in Costa Rica. Cancer Epidemiol Biomarkers Prev. 2004; 13(8):1355-60.
16. Branca M, Giorgi C, Santini D, Di Bonito L, Ciotti M, Costa S, et al. HPV-Pathogen ISS Study Group. Survivin as a marker of cervical intraepithelial neoplasia and high-risk human papillomavirus and a predictor of virus clearance and prognosis in cervical cancer. Am J Clin Pathol 2005; 124(1):113-21.
17. Mueller-Pillasch F., Lacher U., Wallrapp C., Micha A., Zimmerhackl F., Hameister H., et al. Cloning of a gene highly overexpressed in cancer coding for a novel KH-domain containing protein. Oncogene. 1997; 14:2729-2733.
18. Nielsen J., Christiansen J., Lykke-Andersen J., Johnsen A H., Wewer U A., Nielsen F C. A family of insulin-like growth factor II mRNA-binding proteins represses translation in late development. Mol & Cell Biol 1999; 19:1262-1270.
19. Mueller-Pillasch F, Pohl B, Wilda M, Lacher U, Beil M, Wallrapp C, et al. Expression of the highly conserved RNA binding protein KOC in embryogenesis. Mech of Dev 1999; 88:95-99.
20. Nielsen F C, Nielsen J, Christiansen J. A family of IGF-II mRNA binding proteins (IMP) involved in RNA trafficking Scand J Clin Lab Invest Suppl 2001:93-99.
21. Li C, Rock K L, Woda B A, Jiang Z, Fraire A, Dresser K. IMP3 is a novel biomarker for adenocarcinoma in situ of the uterine cervix: an immunohistochemical study in comparison with p16(INK4a) expression. Mod Pathol 2007; 20:242-247.
22. Wang T, Fan L, Watanabe Y, McNeill P D, Moulton G G, Bangur C, et al. L523S, an RNA-binding protein as a potential therapeutic target for lung cancer. British J of Cancer. 2003; 88:887-894.
23. Yantiss R K, Woda B A, Fanger G R, Kalos M, Whalen G F, Tada H, et al. KOC (K homology domain containing 23. protein overexpressed in cancer): a novel molecular marker that distinguishes between benign and malignant lesions of the pancreas. Am J Surg Pathol 2005; 29:188-195.
24. Zheng W, Yi X, Fadare O, Liang S X, Martel M, Schwartz P E, et al. The oncofetal protein IMP3: a novel biomarker for endometrial serous carcinoma. Am J Surg Pathol 2008; 32:304-315.
25. Lu D, Vohra P, Chu P G, Woda B, Rock K L, Jiang Z. An Oncofetal Protein IMP3, A new molecular marker for the detection of esophageal adenocarcinoma and high grade dysplasia. Am J Surg Pathol 2009; 33:521-5.
26. Jiang Z, Chu P G, Woda B A, Rock K L, Liu Q, Hsieh C C, et al. Analysis of RNA-binding protein IMP3 to predict metastasis and prognosis of renal-cell carcinoma: a retrospective study. Lancet Oncol 2006; 7:556-64.
27. Jiang $Z_2$ Lohse C M, Chu P G, Wu C L, Woda B A, Rock K L, et al. The oncofetal protein IMP3: a novel molecular marker that predicts metastasis of papillary and chromophobe renal cell carcinomas. Cancer 2008; 112:2676-268.
28. Hoffmann N E, Sheinin Y, Lohse C M, Cheville J C, Parker A S, Leibovich B C, et al. External validation of IMP3 expression as an independent prognostic marker for metastatic progression and death for patients with clear cell renal cell carcinoma, Cancer 2008; 112:1471-79.
29. Sitnikova L, Mendese G, Liu Q, Woda B A, Lu D, Jiang Z, et al. IMP3 predicts aggressive superficial urothelial carcinoma of the bladder. Clin Cancer Res. 2008; 14(6):1701-6.
30. Liao B, Hu Y, Herrick D A, Brewer G. The RNA-binding protein IMP-3 is a translational activator of insulin-like growth factor II leader-3 mRNA during proliferation of human K562 leukemia cells. J. Biol. Chem. 2005; 280: 1851718524.
31. Yaniv K, Fainsod A, Kalcheim C, Yisraeli J K. The RNA-binding protein Vg1 RBP is required for cell migration during early neural development. Development 2003; 130 (23):5649-61.
32. Vikesaa J, Hansen T V, Jenson L, Borup R, Wewer U M, Christiansen J, et al. RNA-binding IMPs promote cell adhesion and invadopodia formation. EMBO J. 2006; 25(7):1456-68.
33. Merdek K D, Yang X, Taglienti C A, Shaw L M, Mercurio A M. Intrinsic signaling functions of the f34 integrin intracellular domain. J Biol Chem 2007; 282(41):30322-30.
34. Monk B J, Herzog H J. Prevention of cervical cancer and precancerous lesions: the past, present and future: the new era of cervical cancer prevention: HPV vaccination. Gynecologic Oncology. Volume 109, Issue 2, Supplement 1, 2008, p S1-S3.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A method for treating a subject having a cervical squamous intraepithelial lesion (SIL) or cervical intraepithelial neoplasia (CIN), the method comprising the steps of:
   (a) obtaining a sample of SIL or CIN tissue from the subject;
   (b) determining the presence or level of IMP3 protein in the SIL or CIN tissue sample; and
   (c) treating the subject with surgery if the SIL or CIN tissue sample expresses IMP3 protein, or treating the subject with follow-up biopsy and observation if the SIL or CIN tissue sample does not express IMP3 protein.

2. The method of claim 1, further comprising determining at least one other factor, the presence, absence or level of which reasonably correlates with the prediction of invasion from high grade squamous intraepithelial lesion.

3. The method of claim 1, wherein the level of IMP3 protein is compared to a control value, wherein the control value is the level of IMP3 protein in a non-neoplastic cervical tissue of the same subject, or the level of IMP3 protein in a SIL or CIN tissue sample from a subject having a good prognosis.

4. The method of claim 1, wherein determining the presence or level of IMP3 protein comprises immunohistochemical staining.

5. The method of claim 4, comprising using a computerized image analyzer for quantitative analysis.

6. The method of claim 1, wherein the surgery is performed using the loop electrical excision procedure (LEEP).

7. The method of claim 1, wherein the surgery is performed using the cold knife cone excision procedure.

8. A method for monitoring the treatment of a cervical squamous intraepithelial lesion (SIL) or cervical intraepithelial neoplasia (CIN) in a subject, the method comprising determining the presence or level of IMP3 protein in SIL or CIN tissue samples obtained from the subject over time, wherein an increase in the level of IMP3 protein in a later obtained SIL or CIN tissue sample compared to an earlier obtained SIL or CIN tissue sample indicates that the SIL or CIN is becoming invasive cancer.

9. The method of claim 8, wherein determining the presence or level of IMP3 comprises determining the presence or level of IMP3 RNA.

* * * * *